United States Patent
Blew

(10) Patent No.: US 9,927,944 B1
(45) Date of Patent: Mar. 27, 2018

(54) MULTIPLE DELIVERY CHANNELS FOR A DYNAMIC MULTIMEDIA CONTENT PRESENTATION

(71) Applicant: Emmi Solutions, LLC, Chicago, IL (US)

(72) Inventor: Gregory A. Blew, Glen Ellyn, IL (US)

(73) Assignee: Emmi Solutions, LLC, Chicago, IL (US)

( * ) Notice: Subject to any disclaimer, the term of this patent is extended or adjusted under 35 U.S.C. 154(b) by 357 days.

(21) Appl. No.: 14/732,246

(22) Filed: Jun. 5, 2015

Related U.S. Application Data

(60) Provisional application No. 62/084,439, filed on Nov. 25, 2014.

(51) Int. Cl.
| | | |
|---|---|---|
| *G06F 15/16* | (2006.01) | |
| *G06F 3/0481* | (2013.01) | |
| *H04L 29/06* | (2006.01) | |

(52) U.S. Cl.
CPC ............ *G06F 3/0481* (2013.01); *H04L 67/42* (2013.01)

(58) Field of Classification Search
CPC .............................. G06F 3/0481; H04L 67/42
USPC ........................................ 709/219, 225, 226
See application file for complete search history.

(56) References Cited

U.S. PATENT DOCUMENTS

| | | | |
|---|---|---|---|
| 6,248,946 B1 * | 6/2001 | Dwek ............... | G06F 17/30749 434/307 A |
| 6,567,829 B1 | 5/2003 | Ter Horst et al. | |
| 7,734,705 B1 * | 6/2010 | Wheeler, Jr. ......... | G06Q 10/107 709/206 |
| 8,214,518 B1 | 7/2012 | Bertz | |
| 8,838,748 B2 * | 9/2014 | Nair ............................... | 709/203 |
| 9,705,754 B2 * | 7/2017 | Crowder ................. | H04L 41/50 |
| 2002/0010759 A1 * | 1/2002 | Hitson ................... | G06Q 30/02 709/219 |
| 2002/0083187 A1 * | 6/2002 | Sim ................... | G06F 17/30194 709/235 |

(Continued)

OTHER PUBLICATIONS

Adobe Developer Connection, "Creating your first Flash Professional CS5 document," (2010). Retrieved from the Internet on Mar. 10, 2015: <URL:https://adobe.com/devnet/flash/articles/flash_cs5_createfla.html> (2010).

(Continued)

*Primary Examiner* — Phuoc Nguyen
(74) *Attorney, Agent, or Firm* — Marhsall, Gerstein & Borun LLP; Randall G. Rueth

(57) ABSTRACT

According to an embodiment, a designer may utilize an authoring tool to create or edit an interactive media pack ("IMP"). The authoring tool may facilitate creation of multiple versions of an IMP or IMP part. These versions may each be specific to a particular delivery-channel. For example, in an embodiment, a first version may be specific to an IMP presentation made via a graphical user-interface of an application on a mobile device, and a second version may be specific to an IMP presentation made via an interactive voice response system. In some instances, versions for a particular IMP or IMP part may be understood to be linked. That is, progress of an IMP presentation may be tracked so that a user may switch between a first version and second version while losing little, if any, progress in the presentation.

19 Claims, 6 Drawing Sheets

(56) References Cited

U.S. PATENT DOCUMENTS

| | | | |
|---|---|---|---|
| 2004/0117839 A1* | 6/2004 | Watson | H04L 29/06027 725/87 |
| 2004/0122539 A1 | 6/2004 | Ainsworth | |
| 2008/0098319 A1 | 4/2008 | Lucas | |
| 2008/0103371 A1 | 5/2008 | Rosenblum et al. | |
| 2008/0140719 A1* | 6/2008 | Chaney | G06F 17/30053 |
| 2009/0327895 A1 | 12/2009 | Bailloux et al. | |
| 2010/0180011 A1* | 7/2010 | Sood | G06F 15/16 709/219 |
| 2011/0161409 A1* | 6/2011 | Nair | G06F 8/38 709/203 |
| 2014/0244749 A1* | 8/2014 | Martin | H04L 65/602 709/204 |
| 2014/0344453 A1* | 11/2014 | Varney | H04L 41/0803 709/224 |

OTHER PUBLICATIONS

U.S. Appl. No. 14/695,542, filed Apr. 24, 2015, titled "Dynamic Management, Assembly, and Presentation of Web-Based Content".
U.S. Appl. No. 14/712,590, filed May 14, 2015, titled "Environment for Designing a Dynamic Multimedia Content Presentation".

* cited by examiner

MULTIPLE DELIVERY CHANNELS FOR A DYNAMIC MULTIMEDIA CONTENT PRESENTATION

CROSS-REFERENCE TO RELATED APPLICATION

This application claims priority to and benefit of U.S. Provisional Application Ser. No. 62/084,439, which was filed on Nov. 25, 2014 and is titled "Environment for Designing a Dynamic Multimedia Content Presentation," the entire disclosure of which is expressly incorporated herein by reference.

TECHNICAL FIELD

The present disclosure generally relates to dynamic network-based multimedia content presentations.

BACKGROUND

In a typical multimedia presentation, video, audio, and/or text may be presented to an end-user. A typical tool for creating a multimedia presentation generates a file (e.g., an MP4 file or a SWF file) that can be transmitted to a client device so that the client device can play the multimedia content encoded to the file.

SUMMARY

According to an embodiment, a designer may utilize an authoring tool to design and/or edit an interactive multimedia pack (IMP). Generally speaking, an IMP is an application or collection of applications for presenting multimedia content to an end-user via an end-user device. The IMP may include various nodes that may be activated or executed to present a certain subset of the multimedia content associated with the IMP.

According to an embodiment, when authoring an IMP, a designer may utilize an authoring tool to edit the visual and audio content associated with particular nodes. Further, in an embodiment, a designer may utilize an authoring tool to manipulate graphical blocks corresponding to nodes of the IMP. For example, the authoring tool may provide a library of stencils that the designer can utilize to create blocks corresponding to nodes of the IMP. In an embodiment, a designer may link the blocks to create a flow or tree establishing an ordered relationship between the blocks. A set of rules and/or facts may be generated based on the blocks and the designed flow. During IMP presentation, a rules engine may operate to activate nodes of the IMP based on the generated rules and/or facts.

According to an embodiment, an IMP or a part of an IMP ("IMP part") may have multiple versions. These versions may each be specific to a particular delivery-channel. For example, in an embodiment, a first version may be specific to an IMP presentation made via a web client, and a second version may be specific to an IMP presentation made via text-messaging. In some instances, versions for a particular IMP part may be understood to be linked. That is, progress of an IMP presentation may be tracked so that a user may switch between a first version and second version while losing little, if any, progress in the presentation.

DETAILED DESCRIPTION

Figure 1:
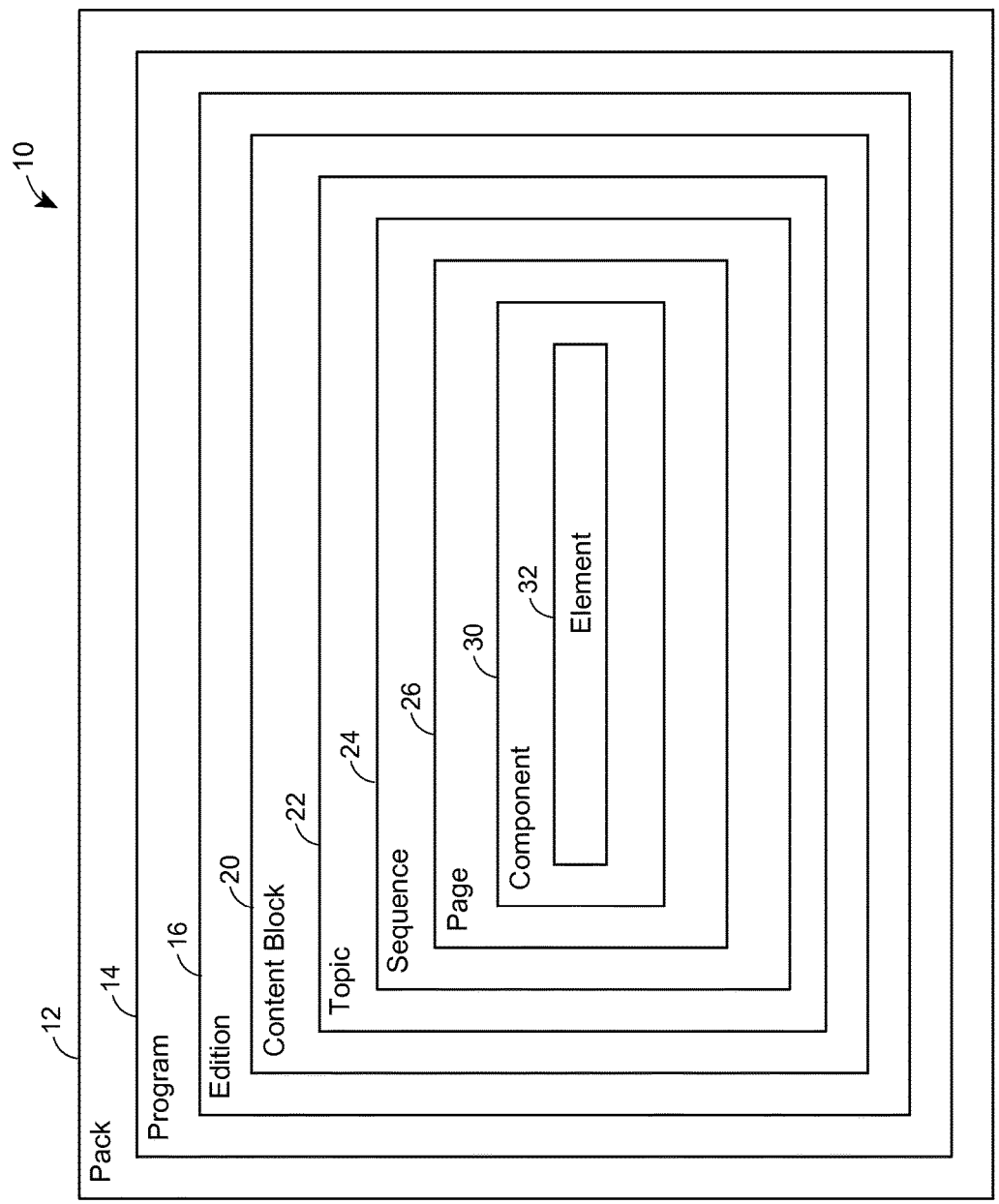
FIG. 1 depicts an example hierarchy for an IMP, according to an embodiment.

Various techniques, systems, and methods are discussed below with reference to FIGS. 1-6. The description below is divided into the following sections:
  I. Overview
  II. An Example IMP Hierarchy
  III. An Example System for IMP Creation and Presentation
  IV. An Example Display
  V. An Example Relational Diagram
  VI. Example Methods
  VII. An Example IMP Authoring System
  VIII. Additional Considerations
  IX. Aspects

I. Overview

Generally speaking, an interactive media pack (IMP) is designed to present multimedia content to a user (generally referred to as an "end-user") via an end-user device (sometimes referred to as a "client device"), or via multiple end-user devices. The IMP may include various nodes that may be activated or executed to present a certain sub-set of the multimedia content associated with the IMP. The IMP may be interactive in nature, allowing an end-user to interact with the presented content. For example, the IMP may prompt the end-user to answer various questions. Further, the IMP may be dynamic in nature. For example, an IMP may include various nodes that may be selectively activated or executed, where each node, if and when activated, may present to the end-user a certain subset of the multimedia content associated with the IMP. Which nodes are activated, and/or the order in which the nodes are activated, may be determined, in whole or in part, during run-time. Accordingly, the particular sequence in which the multimedia content is presented to a user may not be known prior to the IMP being initiated.

The conditional logic used to decide which nodes of an IMP should be next activated may be embodied by "rules." These rules may take any of a number of forms, but generally speaking, may be any information or data that can be referenced for determining what node should be next activated. In an embodiment, one or more of the rules may reside at a third party system. Further, the one or more rules may be implemented, in whole or in part, by a third party system. In other embodiments, none of the rules reside at a third party system, and/or are not implemented by third party systems. To illustrate, the rules may be implemented by a rules engine. Generally speaking, a rules engine is a system configured to select a next node to be activated, for example, according to the rules (i.e., according to logic embodied by the rules) and/or according to other data or information (e.g., "facts"). In an embodiment, the rules engine is implemented, in whole or in part, by a third party. In other embodiments, the rules engine is not implemented by a third party. Regardless of the exact manner of implementation, the rules engine may select a next node for activation according to the rules.

The rules may specify one or more conditions and a particular node to activate when these one or more conditions exists. The existence or non-existence of these conditions may depend on the existence or non-existence of one or more "facts." Thus, to evaluate each condition specified by the rules, the rules engine may access facts stored in a knowledge base and may determine the appropriate node(s) to activate, during run-time, by way of the rules operating on those facts. To illustrate, a rule may stipulate "activate Node X if today is a Tuesday." The condition "today is a Tuesday" depends on a fact: what day of the week "today" actually is. In such an example, the rules engine may access facts in the knowledge base to evaluate the condition "today is a Tuesday," and may activate Node X when the condition is true.

The facts may represent information that was previously provided by the end-user (e.g., in response to user prompts presented earlier within the IMP), and/or information that was collected from other sources (e.g., electronic medical records, patient registry software, prescription software, biometric devices worn by patients, etc.), for example.

The term "nodes," as used herein, may generally refer to units of content of any size or duration, or of variable size and/or duration, within an IMP, and/or to decision points that connect other nodes within the IMP. At a high level, the nodes of the IMP can be understood as belonging to one of four categories: an output-node, an input-node, a decision-point-node, or a collection-node.

Output-nodes generally represent a "page" to be presented to an end-user (e.g., via a display device and/or audio device). Each "page" may include one or more content assets. Examples of these content assets may include an audio content asset and/or a visual content asset (e.g., an image, video, animation, text, or some combination thereof). In some instances, a "page" may be nothing more than text to be presented to a user via text messaging or emailing. Further, in some instances, a "page" may be nothing more than audio to be presented to a user via, for example, an interactive voice response (IVR) system. In some instances, a "page" may include animations, video, text, and/or audio to be presented to a user via, for example, a web-based client.

An input-node generally represents an input prompt to be displayed to an end-user (e.g., a pop-up box including a question and multiple potential answers that may be selected via radio buttons). A decision-point-node generally represents a decision point within the IMP, where the rules engine may evaluate one or more conditions associated with the decision-point-node to determine a next action for the IMP (e.g., to determine which next node to activate). Finally, a collection-node represents a collection of nodes, and may specify a flow between one or more of its constituent nodes. A collection-node may include output-nodes, input-nodes, decision-point-nodes, and even other collection-nodes. Accordingly, the hierarchy and organization of an IMP can quickly become quite complex.

In an embodiment, a particular collection-node (i.e., a node that may include other nodes) may be referred to by a name denoting a particular layer within the hierarchy of an IMP. For example, a particular collection-node may be referred to as a "program," "edition," "content block," "chapter," "topic," "sequence" depending on the overall configuration of the IMP and the level of hierarchy for the particular collection-node in question. As noted, an IMP and its nodes may be arranged according to various configurations or hierarchies, such as a flat configuration, or a hierarchy with nodes at multiple layers (e.g., nodes within nodes). For instance, nodes within one layer of an IMP may include different "programs" that broadly serve different purposes within the IMP (e.g., obtaining advanced directives, obtaining informed consent, facilitating decision-making with respect to a particular health condition, etc.), nodes within a lower layer of the IMP may include different "content blocks" or "chapters" that serve different, more specific purposes within programs (e.g., informing a patient/end-user about a specific subject or asking the patient a subset of questions associated with a subject, etc.), and nodes within a still lower layer of the IMP may include different "pages" that are to be displayed/presented to the end-user within the content blocks or chapters. One example hierarchy, including still more layers, is described below in Section II.

In some embodiments, the dynamic/selective activation (or non-activation) of nodes discussed above occurs within each of multiple hierarchy layers. Referring to the hierarchy examples above (IMP, program, content block, page), for instance, conditional logic may be applied at run-time to determine which page is to be presented next within a particular content block. Similarly, other conditional logic may be applied at run-time to determine which content block is to be presented next within a particular program. Each hierarchy layer may or may not be transparent to the end-user (e.g., depending on whether the presented content includes information that demarks the different nodes within each layer, such as program names, chapter titles, etc.).

Depending on the embodiment, the conditional logic within various layers of an IMP may be understood as a particular type (or category) of conditional logic. For example, the conditional logic may be embodied by rules that facilitate scheduling, and/or rules that facilitate conditional branching. Scheduling may involve activating a node or nodes (and potentially an order for said activation) based on one or more factors (e.g., events or triggers not necessarily expected to occur at any particular time). Conditional branching may involve evaluating conditions at a particular point during execution of an IMP (e.g., at an expected decision-point) to identify a next node for activation from multiple potential nodes. Facts or factors upon which rules for scheduling and/or conditional branching can be based may include, for example: what doctors prescribe to patients; temporal-based events based on schedule, such as reminder calls to watch a program, collect feedback, etc.; special rules and configurations by the hospital or clinic; chaining programs together for illnesses that are related; workflow automation in the context of the above and the extent to which other tasks integrate with other systems (e.g., call systems); information contained within (or derived from) end-user feedback that was provided in response to a user prompt presented earlier in a particular program; etc.

Generally, portions of an IMP may, in some embodiments, be presented to the end-user via one communication channel, or via multiple communication channels. Thus, an IMP may have collection-nodes (e.g., programs, sequences, etc.) designed for a particular communication channel (e.g., for presentation via web browser, text messaging, email, telephone, etc.). For example, a first program within a particular IMP may include multimedia content that is presented to the end-user via a web browser of the end-user's computing device, while a second program of the IMP may include a survey presented to the end-user via email (or via a telephone call using interactive voice response (IVR) technology, etc.).

In some instances, there may exist multiple "versions" of an IMP or of particular portions of an IMP (e.g., of particular programs, chapters, sequences, etc.). These versions may represent substantially the same information that needs to be presented to, or collected from, a user. For example, with reference to the previous example, the first and second program may each be understood as "versions" or "editions" of the same program. Each version may be designed for a particular communication channel. A "monitor" (e.g., implemented by a server) may track the progress of a particular IMP presentation, or of a particular portion of an IMP presentation (e.g., for a particular chapter of an IMP, a sequence of an IMP, a program of an IMP, etc.). The monitor may store progress data representing this progress. This progress data may be referenced to enable transitions between "versions" of an IMP without losing progress in the presentation. For example, in some instances, the progress data may be referenced when presentation of a first version is paused or stopped to "resume" presentation of a second version at a point corresponding to the point where the first version was paused or stopped. In other embodiments, the entire IMP may be presented to the end-user via a single communication channel.

An authoring tool may enable a designer to design and/or edit an IMP. In particular, a designer may utilize an authoring tool to edit the visual and audio content associated with particular nodes. In an embodiment, an authoring tool may include a first interface for editing visual content and a second interface for editing audio content. The first and second interface may exhibit interconnected behavior in some embodiments. For example, when a designer begins working on a particular node in the first interface, the second interface may automatically display relevant information for editing that particular node in the second interface as well (and vice versa).

Further, in an embodiment, a designer may utilize the authoring tool to manipulate graphical blocks corresponding to nodes of the IMP. The authoring tool may provide a third interface for manipulating these graphical blocks. The designer may utilize such an interface to link blocks to create a flow or tree establishing an ordered relationship between the blocks. A set of rules and/or facts may be generated based on the blocks and the designed flow. The third interface may exhibit interconnected behavior with respect to the first and second interface. For example, when a designer begins working on a particular node in the first or second interface, the third interface may display a block corresponding to that particular node, enabling the designer to (i) determine how that particular node relates to other nodes in the flow of the IMP, and (ii) establish a flow between the particular node and the other nodes in the flow of the IMP.

When the IMP is presented, a rules engine may operate to activate nodes of the IMP based on the generated rules and/or facts. When activated, these nodes may cause an end-user device to display certain multimedia content associated with the node.

An authoring tool may be utilized to allow artists, designers, and/or the production team to author programs easily. Program authors (who may also be referred to as 'designers') may drag and drop a sequence of steps (which may be referred to as 'stencils' or 'blocks' below) in a flowchart type network displayed in an authoring tool. Each block may represent a node (e.g., "chapter" or "page") in an IMP flow.

II. An Example IMP Hierarchy 10

FIG. 1 depicts an example hierarchy 10 for an IMP 12, according to an embodiment. The hierarchy 10 includes a program layer 14 with one or more programs of the IMP 12, an edition layer 16 with one or more editions per program, a content block layer 20 with one or more content blocks per edition, a topic layer 22 with one or more topics per content block, a sequence layer 24 with one or more sequences per topic, a page layer 26 with one or more pages per sequence, a component layer 30 with one or more components per sequence, and an element layer 32 with one or more elements per component.

It will be understood that the example hierarchy 10 is a single example hierarchy that an IMP may have in an embodiment, and that an IMP may have a hierarchy different than the hierarchy 10. For example, depending on the embodiment, an IMP may have none of the higher levels of hierarchy. To illustrate, in some instances an IMP may include one or more nodes representing pages, but none of the other collection-nodes displayed in FIG. 1 (i.e., no programs, editions, content blocks, topics, or sequences). In other embodiments, an IMP may include layers of hierarchy above the page layer. In short, an IMP may include any combination of collection-nodes, some or all of which may include other collection-nodes. Thus, the hierarchy of an IMP may be understood as depending on the different collection-nodes existing within an IMP, and the extent to which these collection-nodes include other collection-nodes.

Generally, the IMP 12 may be directed to any type of subject matter, and may serve any type of purpose or purposes relating to that subject matter. For example, the IMP 12 may be designed to facilitate steps of a clinical flow associated with a particular type of medical treatment, therapy or condition. Within the program layer 14, each program may have a particular high-level function, such as obtaining and documenting informed consent (e.g., prior to a surgical procedure for the end-user/patient), obtaining and documenting an advanced directive (e.g., to specify what action should be taken if the end-user/patient is unable to make informed decisions due to health/incapacity issues), providing support for treatment and/or medication decisions, a mix of two or more such functions, etc.

Each of one, some or all of the programs within the program layer 14 may be associated with multiple editions in the edition layer 16. Each edition within a particular program may correspond to a different type of communication channel that is used to convey the program to the end-user. A "communication channel" for a particular edition may refer to the file format of the program content, the file format of instructions specifying the structure and presentation of the program content, and/or the type of end-user device needed to present the program content, for example. To provide some more specific examples, a first edition may correspond to an HTML5 edition of the program intended for presentation on a device with an HTML5-capable browser, a second edition may correspond to an Adobe Flash version of the program intended for presentation on a laptop or desktop computer, a third edition may correspond to an SMS text version of the program intended for presentation on a mobile phone device, a fourth edition may correspond to an IVR version of the program intended for presentation via a mobile or landline phone, and so on. Of course, some types of editions/communication channels may be unsuitable for particular programs (e.g., an IVR edition may be unsuitable for a program that heavily relies on video content), and/or some or all programs within the program layer 14 may only be associated with a single edition.

Each content block within the content block layer 20 may have a particular function, such as providing background information to the end-user, collecting information from the end-user (e.g., demographic information, information reflecting a self-assessment of symptoms, etc.), providing results to the end-user (e.g., based on information that the end-user entered earlier in the program), taking a particular action (e.g., scheduling a follow-up appointment, providing or setting up a reminder, sending results to healthcare professionals, etc.), a mix of two of more such functions, or any other suitable function.

Each topic within the topic layer 22 may have a more specific function within its respective/parent content block, such as providing a particular subset of background information to the end-user, collecting a particular subset of information from the end-user, etc. In some embodiments, topics may be the only divisions of an IMP that are noticeable to the end-user, with all other layers of the hierarchy 10 being transparent to the end-user.

Each sequence of the sequence layer 24 may contain an animation, a series of images and/or text, and/or other temporally-varying visual and/or audio content. A single sequence may contain a number of pages from the page layer 26, where each page arranges one or more components in the component layer 30 according to a layout specific to that page. In some embodiments, the layout of each page is dependent on the display capabilities of the end-user device (e.g., the aspect ratio of the display screen). Each component of a page may be a collection of one or more visual and/or audio elements within the element layer 32 (e.g., blocks of text, snippets of audio or video, etc.).

Some of the nodes/units within one or more of the layers of the example hierarchy 10 may be reusable. For example, a content management system may store a number of different topics, each of which can be retrieved and plugged into different content blocks and/or different IMPs. As another example, the content management system may store a number of different content blocks, each of which can be retrieved and plugged into different programs and/or different IMPs.

It is understood that, in other embodiments/implementations, the hierarchy 10 may include more, fewer and/or different layers than those shown in FIG. 1. Moreover, a single IMP may be viewed as having multiple different hierarchical configurations (e.g., by grouping the content of the IMP in various different ways).

III. An Example System 100 for IMP Creation and Presentation

Figure 2:
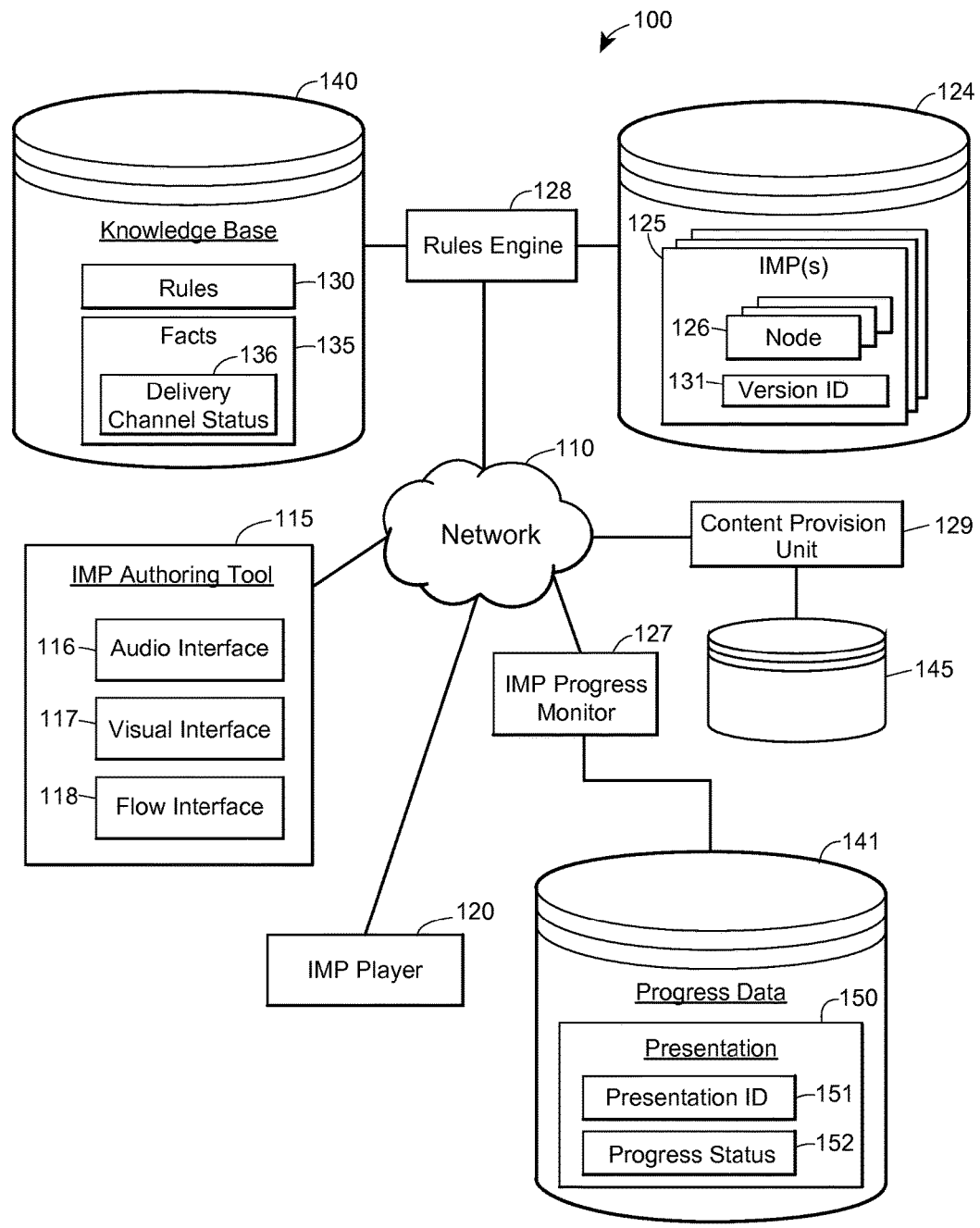
FIG. 2 depicts a block diagram of an example system for creating and presenting IMP(s), according to an embodiment.

FIG. 2 depicts a block diagram of an example system 100 for creating and presenting IMP(s) 125.

In an embodiment, the system 100 includes a network 110, an IMP Authoring Tool 115, an IMP Player 120, an IMP progress monitor 127 (referred to herein as "monitor 127"), a rules engine 128, a content provision unit 129, a database 124 storing data for one or more IMPs 125, a knowledge base 140, a database 141 storing progress data, and a content database 145.

The knowledge base 140 may include one or more databases storing rules 130 and facts 135. The facts 135 may include a delivery-channel status 136.

Generally speaking, each IMP 125 within the database 124 represents a particular collection of nodes 126. Thus, the database 124 may include one or more nodes 126, various subsets of which may correspond to particular IMPs 125. Each IMP 125 may include one or more version IDs 131. Each version ID 131 may be any piece of information or data (e.g., a variable value) that identifies a version of an IMP or IMP part and, therefore, corresponds to the delivery-channel by which the IMP or IMP part is intended to be delivered. In short, the version ID 131 enables multiple versions of an IMP part to be distinguished from one another, and may take any of a number of forms depending on the embodiment. It will be appreciated that in some embodiments, one or more (or even all) IMPs 125 do not include a version ID 131.

The progress data 141 may include data for one or more presentations(s) 150. For example, for each presentation 150, the progress data 141 may include (i) a presentation ID 151 to identify the particular presentation 150 being tracked, and (ii) a progress status variable 152, the value of which reflects the progress of the tracked presentation 150. In an embodiment, some or all of the progress data 141 may be included as facts 135 in the knowledge base 140.

Each of the IMP Authoring Tool 115, the IMP Player 120, the monitor 127, the rules engine 128, and the content provision unit 129 may reside on a computing device. For example, the monitor 127, the rules engine 128, and the content provision unit 129 may reside on the servers 620 shown in FIG. 6. In an embodiment, the monitor 127, the rules engine 128, and the content provision unit 129 are each implemented by a different server. In another embodiment, the monitor 127, the rules engine 128, and content provision unit 129 are all implemented by a single server. In another embodiment, two of the monitor 127, the rules engine 128, and content provision unit 129 are implemented on a first server, while the other is implemented on a second server.

Each of the IMP Authoring Tool 115, IMP Player 120, the monitor 127, the rules engine 128, and the content provision unit 129 may be coupled to the network 110. The network 110 may be any suitable network, including wireless and/or wired links.

(A) IMP Player 120 and Presentation of the IMP 125

The IMP Player 120 is a tool for presenting the IMP 125. Generally speaking, the IMP Player 120 may be one or more instructions, routines, modules, processes, services, programs, and/or applications that when executed by a processor cause a display device to present a graphical user-interface (GUI) to a user ("end-user) to enable the end-user to "play" the IMP 125. Some embodiments do not include a dedicated IMP Player 120, and/or include one or more other general-purpose software and/or end-user devices in addition to an IMP Player 120. For example, in some instances an IMP 125 may be presented to a user, in whole or in part, via text messaging and/or emailing.

The rules engine 128 is a tool for identifying one or more next nodes of the IMP 125 to be presented during run-time. Generally speaking, the rules engine 128 may be one or more instructions, routines, modules, processes, services, programs, and/or applications that when executed cause a processor to evaluate one or more rules 130 and/or facts 135 in the knowledge base 140 and to identify a next node or nodes 126 for presentation.

The content provision unit 129 is a tool for content delivery. Generally speaking, the content provision unit 129 may be one or more instructions, routines, modules, processes, services, programs, and/or applications that when executed cause a processor to retrieve content assets from the content database 145 and to transmit the retrieved content assets to the IMP Player 120.

Generally speaking, the nodes 126 are data corresponding to particular subsections or modular portions of the IMP 125 that may be presented via the IMP Player 120. The nodes 126 (or node data 126) may include executable instructions or routines representing these particular subsections or modular portions of the IMP 125. Each node 126 generally represents an output to be displayed via a GUI of the IMP Player 120, (e.g., a page including one or more multimedia content assets), an input prompt to be displayed via a GUI of the IMP Player 120, or a decision point at which point the rules engine 128 will select a next node 126 for activation from multiple potential next nodes. The node data 126 may include HTML5 instructions that specify, for each node, the content asset(s) that is/are to be presented, as well as the presentation of that content. For example, the HTML5 instructions may specify the layout(s), font(s), and/or one or more other characteristics for each content asset within each presented page/screen within a given node.

In example operation, the IMP Player 120 presents multimedia content to the end-user according to the nodes 126 of the IMP 125, each of which may reference or include particular multimedia content. The particular nodes 126 to be played, and the order in which they are played, may be determined by the rules engine 128.

In particular, the rules engine 128 may evaluate one or more of the rules 130 and/or facts 135 in the knowledge base 140, and may identify a next node or nodes 126 for presentation based on that evaluation. In an embodiment, the rules engine 128 may evaluate a rule 130, but not a fact. For example, in an embodiment, a rule 130 may simply stipulate "Activate Node Z after Node Y." The multimedia content associated with each node 126 may be referred to as a "content asset." The content assets may be stored at the content database 145, and may be retrieved by the content provision unit 129 and transmitted to the IMP Player 120. An example content asset may be or may include an element in the element layer 32 shown in FIG. 1, and/or a component in the component layer 30 shown in FIG. 1.

In an embodiment, the rules engine 128 may transmit the identity of the identified next node 126 to the IMP Player 120. The content provision unit 129 may provide the content asset(s) associated with the identified next node 126, alone or in a group with the content assets of one or more other nodes 126. The content provision unit 129 may send content only upon request from the IMP Player 120, or without waiting for a request, in different embodiments. In an embodiment, the rules engine 128 may also transmit the identity of the identified next node 126 to the content provision unit 129. The content provision unit 129 may then reference the node data 126 to identify the appropriate content assets associated with the identified next node 126, and may transmit the appropriate content assets to the IMP Player 120. Alternatively, the rules engine 128 may reference the node data 126 to identify the appropriate content assets associated with the identified next node 126, and may communicate with the content provision unit 129 to cause the content provision unit 129 to transmit the appropriate content assets to the IMP Player 120.

In some instances, some of the nodes 126 are organized into groups that may be referred to as "collection-nodes." These collection-nodes may be referred to as "programs," "editions," "content blocks," "chapters," "topics," or "sequences" depending on the overall configuration of the IMP 125 and the level of hierarchy for the particular collection-node in question. The order in which the IMP Player 120 presents the multimedia content associated with the nodes 126 may be determined based on the rules 130 and facts 135 in the knowledge base 140.

When the IMP 125 is presented via the IMP Player 120, the nodes 126 may be activated according to an order specified by the rules engine 128. The rules engine 128 may determine the order of activation based on rules 130 and facts 135 in the knowledge base 140. The rules 130 and/or facts 135 may be defined according to user input entered via the IMP Authoring Tool 115 (e.g., a designer creating rules and/or specifying facts) and/or via the IMP Player 120 (e.g., an end-user providing an answer to a query that is then inserted into the knowledge base 140 as a new fact).

Generally, each rule 130 specifies a condition and an action. When the rules engine 128 fires, it may evaluate one or more rules 130 and/or one or more facts 135 to determine whether one or more condition(s) specified by the one or more rules 130 are true. If a condition is true, the corresponding action is initiated. The action may specify a node 126 or program (e.g., a collection of nodes 126) to activate. For example, a rule 130 may specify a condition (e.g., a person is a smoker) and an action to initiate if the condition is true (e.g., initiate a 'stop smoking' node 126). The rules engine 128 generally evaluates a rule 130 based on the facts 135 (e.g., a 'smoker' variable may exist to indicate whether a particular person is a smoker). In some instances, the action may specify a new fact 135 to insert into the knowledge base 140. For example, if a needed fact 135 does not exist or has not been defined, an input prompt may be activated to request user-input that can be used to define a new fact 135. In short, it could be said that the defined rules 130 specify various conditions for determining which of the potential next nodes 126 should be activated.

A fact 135 is generally a variable or attribute value. For example, a fact 135 may indicate the existence of various diseases or disorders (e.g., diabetes, heart disease, cancer, etc.) or identify demographic information for a person (e.g., gender, blood type, height, weight, age, etc.).

In some instances, one or more rules 130 may indicate that a particular version of an IMP (or of an IMP part) is to be presented if certain conditions are true. A version for a particular IMP (or IMP part) may be determined based on a version ID 131 associated with the particular IMP (or IMP part). As noted above, the version ID 131 may be any piece of information or data (e.g., a variable value) that identifies a version of an IMP or IMP part. That is, an IMP 125 may have multiple versions, and the version ID 131 may distinguish one version of the IMP 125 from a second version of the IMP 125. Further, a collection-node may represent a particular version of an IMP part, and may have an associated version ID 131 to distinguish one version of an IMP part from a second version of an IMP part. For example, a program of an IMP 125 may have multiple versions, and the version ID 131 may distinguish one version of the program from a second version of the program. In an embodiment, the version ID 131 may be a combination of alphanumeric characters unique to a particular version. For example, a version ID 131 for a first IMP part may be "WEB" or "V1," and a second version ID 131 for a second IMP part may be "IVR" or "V2."

As noted, one or more rules 130 may be evaluated to determine which version of an IMP or IMP part is to be presented. For example, the one or more rules may indicate that when a first delivery-channel is active or selected, a first version is to be presented. The terms "active" and "selected" are generally used interchangeably when used with reference to a delivery-channel. A delivery-channel may be said to be selected or active when it is being used to present the IMP, or will be used for presentation. For example, a user may interact with a client device to initiate a particular type of IMP player, which may result in the selection or activation of a delivery-channel corresponding to the IMP player type. For example, if the IMP 125 is being presented via text message, the delivery-channel status 136 may indicate that text messaging is the active delivery-channel. If the IMP 125 is being presented via a web-based client, the delivery-channel status 136 may indicate that the web-based client is the active delivery-channel. The delivery-channel status 136 may be set based on communication with the IMP Player 120.

Similarly, the one or more rules 130 may indicate that when a second delivery-channel is active or selected, a second version is to be presented. In an embodiment, the active/selected delivery-channel may be identified by referencing the delivery-channel status 136. Thus, it may be said that in certain embodiments, a version of a particular IMP or IMP part is correlated with a particular delivery-channel (or delivery-channel status 136) via one or more rules 130 in the knowledge base 140.

(B) Progress Monitor 127 and Tracking Presentations of a IMP 125

Progress data 141 may be referenced to enable (i) the stopping and resuming of an IMP 125, and (ii) transitioning between "versions" of an IMP 125 or IMP 125 part without losing progress in the presentation. The progress data 141 may be managed by the monitor 127.

The monitor 127 is a tool for monitoring progress of a presentation of the IMP 125. That is, the monitor 127 may operate to track how much of the IMP 125 has been presented for a particular presentation. Each IMP 125 may be presented multiple times. For example, a first IMP 125 may be presented via a first presentation and a second presentation. The first presentation and second presentation may occur at the same IMP Player 120, or at different IMP Players 120. Further, a second IMP 125 (which may include different nodes 126 than the first IMP 125), may be presented multiple times. In short, each IMP 125 represents a particular collection of nodes 126 that can be presented via an IMP Player 120, and each presentation of an IMP 125 represents a particular instance of that IMP 125 being presented via an IMP Player 120.

The monitor 127 may track progress by updating the progress data 141 to reflect the progress of a particular presentation. Further, the monitor 127 may access the progress data 141 to determine how a particular presentation has progressed (e.g., to determine where a paused presentation needs to resume). The progress data 141 may include progress data for multiple presentations 150. For example, for each presentation 150 tracked by the monitor 127, the progress data 141 may include (i) a presentation ID 151 to identify the particular presentation 150 being tracked, and (ii) a progress status variable 152, the value of which reflects the progress of the tracked presentation 150.

Generally speaking, a presentation ID 151 is a value unique to a particular presentation. For example, when an end-user utilizes an IMP Player 120 to start a new presentation, the monitor 127 may generate a new presentation ID 151. The presentation ID 151 may be a randomly generated value. In some instances, the presentation ID 151 may be generated based on information unique to the presentation. For example, the presentation ID 151 may be based on a value unique to a particular IMP Player 120 presenting the IMP 125 (e.g., a key or hash associated with every installation of a IMP Player 120). As another example, the presentation ID 151 may be generated based on a user ID unique to the end-user (e.g., a username) and/or unique to the client-device used by the end-user (e.g., a MAC address for the client device). Regardless of how the presentation ID 151 is generated, it can be used to store and access a progress status 152 for a particular presentation of a IMP 125.

The progress status 152 may be any data or variable value representing a status of the presentation 150. In some instances, the progress status 152 may identify the most recent node 126 to be played by the IMP Player 120. In other instances, the progress status 152 may be a number representing a percent or fraction of a total (e.g., wherein the total corresponds to a complete presentation).

The progress data 141 may be referenced to facilitate transitioning between "versions" of an IMP 125 or IMP 125 part without losing progress in the presentation. For example, in an embodiment, one or more of the rules 130 may specify a first version of an IMP part (e.g., one or more nodes) to be activated when first conditions are met and a second version of an IMP part (e.g., one or more nodes) to be activated when second conditions are met. These conditions may reference the delivery-channel status 136. For example, the one or more rules 130 may specify that the first version is to be activated when a first delivery-channel is active or selected, and that the second version is to be activated when a second delivery-channel is active or selected. Thus, presentation of an IMP 125 may seamlessly transition between versions of an IMP or IMP part based on the delivery-channel.

As another example, a presentation 150 of a first version of an IMP 125 may begin, and the monitor 127 may update the progress data 141 to track the progress of the presentation. In particular, the monitor 127 may update a progress status 152 associated with a presentation ID 151 unique to the presentation 150.

During the presentation, the rules engine 128 may evaluate one or more rules 130 to identify one or more next nodes for presentation. The evaluation of the one or more rules 130 may indicate that nodes from a second version of the IMP are to be presented. The nodes from the second version may be selected and transmitted to the IMP Player 120 for presentation. In an embodiment, the rules engine 128 references the progress status 152 for the presentation 150 to determine which particular nodes in the second version are to be presented. That is, the progress status 152 may be utilized to essentially resume presentation without starting the second version of the IMP 125 from the beginning. In an embodiment, the one or more rules 130 specify the particular nodes from the second version to be presented, and the rules engine 128 selects those particular nodes for presentation without reference to the progress status 152.

(C) IMP Authoring Tool 115 and Creation of the IMP 125

The IMP Authoring Tool 115 may be utilized to generate or define the rules 130 and/or facts 135. Generally speaking, the IMP Authoring Tool 115 may be one or more instructions, routines, modules, processes, services, programs, and/or applications that when executed by a processor cause a display device to present one or more graphical user-interfaces (GUIs) to enable a user of the IMP Authoring Tool 115 ("designer") to create and/or manipulate (e.g., via user-input) the design of the IMP 125.

The IMP Authoring Tool 115 may include one or more components or parts: an audio interface 116, a visual interface 117, and/or a flow interface 118. Generally speaking, the audio interface 116 and visual interface 117 enable a designer to select or define content that will be presented when one or more particular nodes 126 of the IMP 125 are presented during presentation of the IMP 125. By comparison, the flow interface 118 enables a designer to define a flow between nodes 126 of the IMP 125, wherein the flow generally corresponds to an order for presenting the nodes 126 during presentation of the IMP 125. Accordingly, the flow interface 118 might be considered a "high-level" editor when compared to the audio interface 116 and visual interface 117. In an embodiment, the audio interface 116, visual interface 117, and flow interface 118 may exhibit interconnected behavior. For example, when a designer edits a particular node 126 in one of the interfaces, the other interfaces may display relevant information for the particular node 126 (e.g., so that a designer can easily access and/or edit audio, visual, and flow information for a particular node).

(1) Audio Interface 116

The audio interface 116 may be displayed at a display device to a designer. In short, the audio interface 116 enables the designer to define or select audio to be presented when a particular node 126 or set of nodes 126 of the IMP 125 is presented to an end-user during presentation of the IMP 125. For example, a designer may utilize the audio interface 116 to define particular audio to be presented (e.g., via a speaker) when a particular page of the IMP 125 is presented.

In an embodiment, the displayed audio interface 116 includes a text field for defining audio to be presented when a particular page is presented. The designer may enter text in the text field. The provided text may be converted to audio using a text-to-speech tool. In some instances, a person might record audio of himself or herself reading the provided text. In either event, the audio may be stored to memory as associated with the particular page.

In an embodiment, the audio interface 116 includes an input element (e.g., a button) that the designer may interact with to cause the IMP Authoring Tool 115 to record audio. The designer might then record (e.g., via a microphone) audio that he or she desires to be presented with the particular page. Such an embodiment may not require text entry.

In some embodiments, the audio interface 116 displays multiple audio files from which the designer can choose. Regardless of how the audio has been defined (i.e., whether defined via text entry, audio recording, file selection, or some other means of audio selection/definition), the IMP Authoring Tool 115 may store to memory data for the particular page (e.g., as node data 126) referencing the defined audio, so that the stored data may be later referenced to identify the defined audio as associated with the particular page the designer was editing via the audio interface 116.

(2) Visual Interface 117

The visual interface 117 may be presented at a display device to a designer. The visual interface 117 enables the designer to define or select visual elements to be displayed when a particular node 126 or set of nodes 126 of the IMP 125 is presented to an end-user during presentation of the IMP 125. For example, the designer may utilize the visual interface 117 to define particular visuals (e.g., text and/or images) to be presented (e.g., via a display device) when a particular page of the IMP 125 is presented.

In an embodiment, the displayed visual interface 117 includes a "design area" (which may be referred to as a "visual design area") where a designer may place visual elements to be displayed when a particular page is displayed. In some instances, the visual interface 117 may include a library area where various images or image identifiers are displayed. These images or image identifiers may be "dragged and dropped" into the design area. In some instances, the visual interface 117 may include an input element (e.g., a button, toolbar menu, or some other interactive graphic element) that a designer may interact with to activate the library (i.e., to cause the visual interface 117 to display the library). In any event, the IMP Authoring Tool 115 may store to memory data for the particular page (e.g., as node data 126) that references the visual element(s) that have been placed in the design area, so that the stored data may be later referenced to identify selected visual elements as associated with the particular page the designer was editing via the visual interface 117.

(3) Flow Interface 118

The flow interface 118 may be presented at a display device to a designer. The flow interface 118 enables the designer to define or select a flow between nodes 126 of the IMP 125. In short, this flow defines the particular nodes 126 to be presented (or potentially presented) during presentation of the IMP 125, as well as an order or potential order(s) in which the nodes 126 are to be presented. While the exact determination regarding node-selection and order of presentation may not be known until run-time (because node-selection and order of presentation may depend on conditions and facts that are not evaluated until run-time), the flow defines a broad structure or outline for presentation of the IMP 125.

In an embodiment, the displayed flow interface 118 includes a "design area" (which may be referred to as a "flow design area") where a designer may place blocks or icons representing nodes 126 of the IMP 125, which may include, e.g., output-nodes, input-nodes, decision-point-nodes (corresponding to conditions to be evaluated at run-time), and/or collection-nodes. Further, a designer may utilize a design area of the flow interface 118 to define connections between the blocks or icons representing the nodes 126. These placed blocks or icons, and the connections between them, generally define a flow. The defined flow may be used to add, edit, and/or delete rules 130 and/or facts 135 in the knowledge base 140.

Accordingly, using the flow interface 118, the designer can add, edit, and/or delete rules 130 and/or facts 135 that will be utilized by the rules engine 128 during runtime to identify a next node 126 for execution. The designer can make these changes by adding, removing, or editing node icons or blocks in a "design area" of the flow interface 118. Each created block corresponds to a particular node 126. The node icons or blocks may be pulled from a library in the IMP Authoring Tool 115. Further, the designer may link the blocks, creating a block tree. The rules 130 may be created/defined based on the blocks and block tree designed by the designer. Accordingly, the IMP Authoring Tool 115 enables the designer to create a sequence of linked blocks, representing a hierarchy or potential "flow" of nodes 126 to be activated when the IMP 125 is presented via the IMP Player 120.

In some instances, the flow interface 118 displayed by the IMP Authoring Tool 115 may include a library of preconfigured blocks, which may be referred to as "stencils." A stencil may be understood as template block. A stencil may be placed in the design area to create a block from the stencil. In some instances, the designer may assign certain attributes or values to the block (e.g., specifying particular multimedia content that will be presented when the node 126 corresponding to the created block is activated). For example, the library may include a radio-button user-input stencil. The designer may drag the stencil into a "design area," where the designer may bind various attributes and/or attribute values to the stencil to define a particular node. For example, the designer may specify particular text that defines the question that will be asked when the node is activated. Similarly, the designer may specify an attribute that will be defined based on the input provided by the end-user.

As another example, a designer using the IMP Authoring Tool 115 may create a block corresponding to a decision node 126 that has two branches leading to first and second potential next blocks. The designer may define a condition (e.g., variable XYZ has the value 'TRUE') for a rule 130, where the branches stemming from the created block represent the actions for the rule 130. Thus, when the IMP 125 is initiated for presentation to an end-user and the decision node 126 corresponding to the created block is activated, the rules engine 128 may (i) initiate a first action (e.g., a first node 126 is activated) when the condition is true (e.g., XYZ='TRUE'); and (ii) initiate a second action (e.g., a second node 126 is activated) when the condition is false (e.g., XYZ='FALSE' or null).

In some instances, the designer may create a block so that an input prompt is generated and the condition of the corresponding rule 130 depends on the end-user's input (which may also be inserted into the knowledge base 140 as a new fact 135). In other words, the selection of a next node 126 for activation may depend on end-user input. It will be understood that the above examples are illustrative and that the IMP Authoring Tool 115 may be used to define a rule 130 with other conditions and actions.

In some instances, the designer may designate, via the flow interface 118, a particular flow-definition as a collection-node (e.g., a program or chapter). The designer may specify a particular level of hierarchy within the IMP 125 for such a flow-definition. As an example, the designer may create a "topic" that comprises a first sequence of "pages" and a second sequence of "pages." As another example, the designer may create a "content block" that includes a first "topic" and a second "topic." For example, the first topic may relate to a first health issue (e.g., high blood pressure) and the second topic may relate to a second health issue (e.g., a particular blood pressure medication). To further illustrate, a designer may create a first and second program for a particular IMP 125. Further, for one or more of the first and second program, the designer may create multiple "versions." These program versions are sometimes referred to as "editions." Thus, each program may have multiple "versions" or "editions."

The designer may utilize the flow interface 118 to create "versions" of not only programs, but of other collection-nodes within the IMP 125. For example, an IMP 125 itself may have multiple "versions." Similarly, a content block, topic, and/or sequence may have multiple "versions." Generally, each version of a collection-node represents substantially the same goal regarding information communicated to, and collected from, an end-user for the particular collection-node(s) represented by the multiple "versions."

Each version created by a designer may be particular to a specific type of IMP Player 120 or client device. To illustrate, a designer may create a first flow-definition for a version meant to be presented via a client device that is a desktop computer. The designer may create a second flow-definition for a version meant to be presented via a client device that is a mobile phone or tablet. The rules engine 128 may determine which version to present via the client device based on the client device type. In some instances, a designer may create a flow-definition meant to be presented via text messages to a client device. In such instances, the flow-definition may consist of pages including text and/or images formatted for presentation via text messaging (e.g., the images may be a lower resolution, and thus smaller in file size).

In short, it may be said that the IMP Authoring Tool 115 enables a designer to "program" an IMP 125. Importantly, such "programming" does not require a great deal of experience or skill, and thus may enable non-programmers to "program" an IMP 125. After the IMP 125 has been edited or created, its contents may be stored at a memory device. In an embodiment, the contents of the IMP 125 are stored at a database or memory device accessible via the network 110. In some embodiments, one or more servers may provide the contents of the IMP 125 to an end-user device via the network 110.

IV. An Example Display 300

Figure 3:
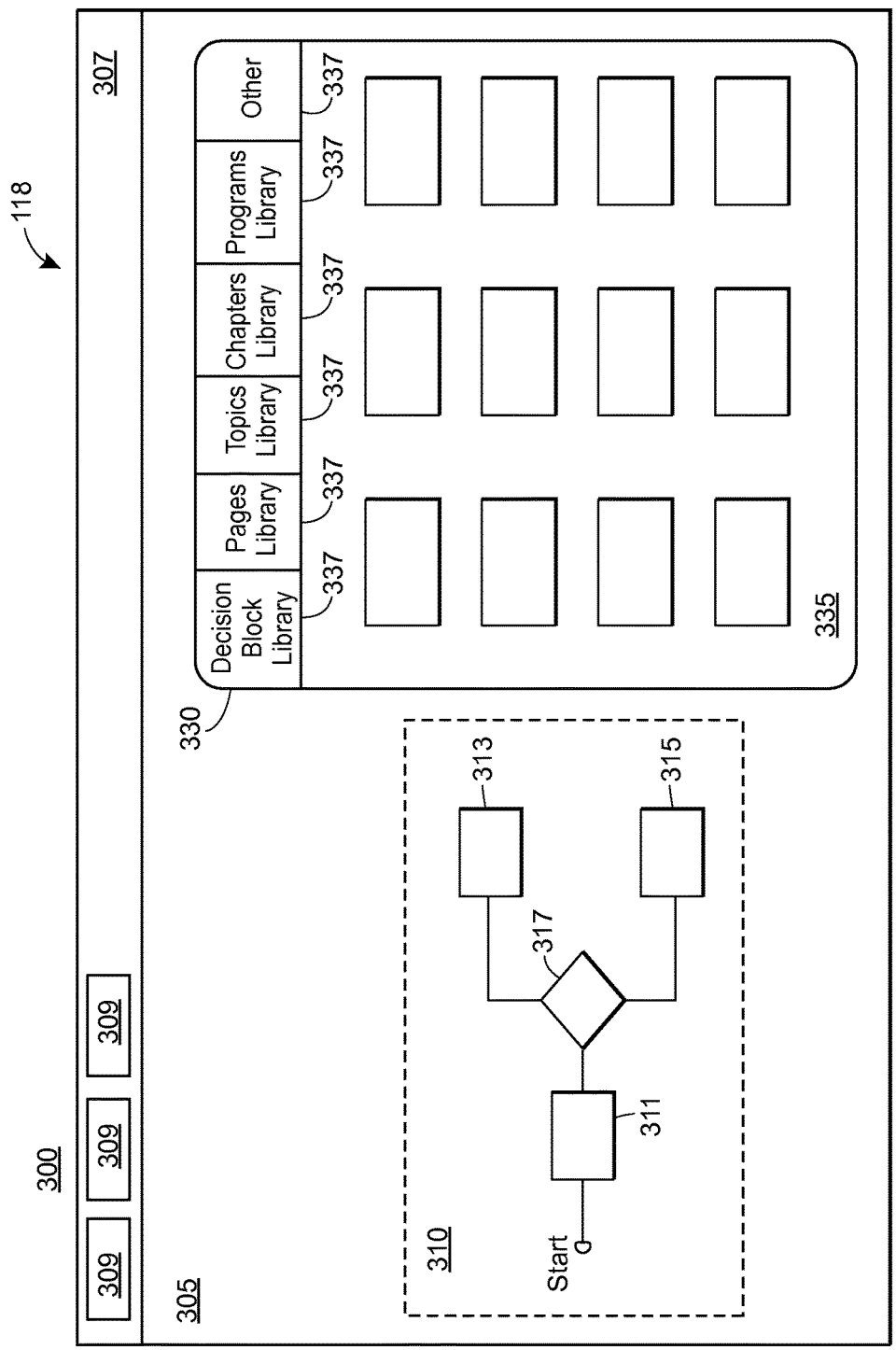
FIG. 3 depicts an example display that may be provided by a display device when a flow interface is displayed, according to an embodiment.

FIG. 3 depicts an example display 300 that may be provided by a display device when the flow interface 118 is displayed, according to an embodiment. It will be appreciated that in some embodiments the flow interface 118 may be displayed simultaneously with the audio interface 116 or the visual interface 117. In some embodiments, the audio interface 116, visual interface 117, and flow interface 118 may all be displayed at the same time via a single display device or group of display devices.

In an embodiment, the flow interface 118 may include a design area 305 and/or a toolbar 307. As depicted, the design area 305 includes a block tree 310 (generally referred to herein as a flow-definition 310) and a library 330.

Generally speaking, a designer may specify nodes 126 to be included in the IMP 125 by placing "blocks" (i.e., graphical representations of the specified nodes 126) in the design area 305. The designer may then connect the blocks to establish the flow-definition 310 for the IMP 125. Thus, the flow-definition 310 is defined according to the blocks 311-317 and the links connecting the blocks 311-317.

In some instances a flow-definition 310 may include a single block. In other instances, a flow-definition 310 may include multiple blocks. In short, the flow-definition 310 defines nodes 126 to be potentially activated during runtime of the IMP 125, as well as a potential order for activating the nodes 126. More particularly, the IMP Authoring Tool 115 (shown in FIG. 2) may populate the knowledge base 140 (shown in FIG. 2) with rules 130 and/or facts 135 according to the flow-definition 310 specified by the designer. During run-time of the IMP 125, the rules engine 128 may identify the next node or nodes 126 to activate by evaluating, during run-time, the rules 130 and/or facts 135 in the knowledge base 140. The identity of the next node or nodes 126 may be communicated to the content provision unit 129 (shown in FIG. 2), and the content provision unit 129 may transmit the content associated with the next node or nodes 126 to the IMP Player 120.

One or more of the blocks 311-317 may correspond to collection-nodes. For example, one or more of the blocks may represent programs, topics, or sequences. In some instances, a designer may "navigate" through various layers of an IMP. In an embodiment, for example, a user may "select" a particular block corresponding to a collection-node (e.g., by double clicking on the particular block), which may result in the flow interface 118 displaying blocks corresponding to nodes within the collection-node corresponding to the selected block. Thus, a designer may navigate through the various layers of hierarchy that an IMP 125 may have, enabling the designer to view the nodes and flow-definitions for collection-nodes in layers above and/or below the layer he or she is viewing at any particular time.

One or more of the blocks 311-317 may correspond to output-nodes. For example, one or more of the blocks may represent pages to be presented via the IMP Player 120. The designer may design these pages by selecting one or more multimedia content assets to be presented with the page (e.g., by utilizing the audio interface 116 or visual interface 117).

One or more of the blocks 311-317 may correspond to input-nodes. That is, one or more of the blocks may be input-prompt blocks (sometimes referred to as rule blocks or rule definition blocks) used to design an input-prompt graphic (e.g., asking the user to answer a question) to be presented when a node 126 corresponding to the input-prompt block is activated. The designer may specify the prompt and/or variables (i.e., facts) that may be defined based on the end-user's answer. Because an input-prompt block may be used to generate or define a new fact, it may be understood as a rule (which may be stored in the knowledge base) for obtaining a new fact. For example, the designer may specify text for the input-prompt block 521 such as "What is your blood type?" The designer may further specify text to be associated with radio buttons so that an end-user may answer the question (e.g., "A–," "O+," etc.). When a node 126 presents the input-prompt corresponding to the input-prompt block 521, the received answer may be inserted into the knowledge base 140 as a new fact.

Further, one or more of the blocks 311-317 may correspond to decision-point nodes. For example, block 317 is a decision block. The decision block 317 may be utilized to introduce branching in the flow-definition 310. A designer may introduce branching so that the selection of nodes 126 during IMP presentation depends on rules and/or facts in the knowledge base 140. To configure the flow-definition 310 so that node activation during presentation of the IMP 125 depends on a fact, a designer may bind or associate the fact with the decision block 317. For example, a designer may bind an age variable with the decision block 317, where the blocks 313 and 315 correspond to potential next nodes to be activated after the node associated with block 311, depending on a value for the age variable. For example, the decision block 317 may stipulate that the node corresponding to the block 313 is to be activated when the value is 0-29, and that the node corresponding to the block 315 is to be activated when the value is 30 or greater. During presentation of the IMP 125, the rules engine 128 may determine the value of the age variable by referencing the knowledge base.

It will be appreciated that, depending on the particular flow-definition 310 for an IMP 125, the IMP 125 may not necessarily activate every node 126 represented by the blocks placed in the design area 305. For example, the depicted flow-definition 310 includes blocks 311-317. Because block 317 is a decision block, the IMP 125 (as defined in this particular example) may not activate both nodes represented by blocks 313 and 315. Rather, for this particular example, during execution of the IMP 125, the rules engine 128 (shown in FIG. 1) may evaluate the rules and facts in the knowledge base 140 (populated, as noted, based on the flow-definition 310) to determine which of the nodes corresponding to the blocks 313 and 315 to activate.

While the exact determination regarding node-selection and order of presentation may not be known until run-time (because node-selection and order of presentation may depend on conditions and facts that are not evaluated until run-time), the flow defines a broad structure or outline for presentation of the IMP 125.

The library 330 includes tabs 337 and stencils 335. The stencils 335 essentially represent pre-configured nodes. For example, a stencil may represent a page or program that has already been designed or configured to a certain extent. Some stencils 335 may require further configuration. Other stencils 335 may not require further configuration. A designer may add blocks to the design area 305 by dragging stencils 335 from the library 330 and dropping them onto the design area 305. The tabs 337 may specify categories or types of stencil 335.

V. An Example Relational Diagram 400

Figure 4:
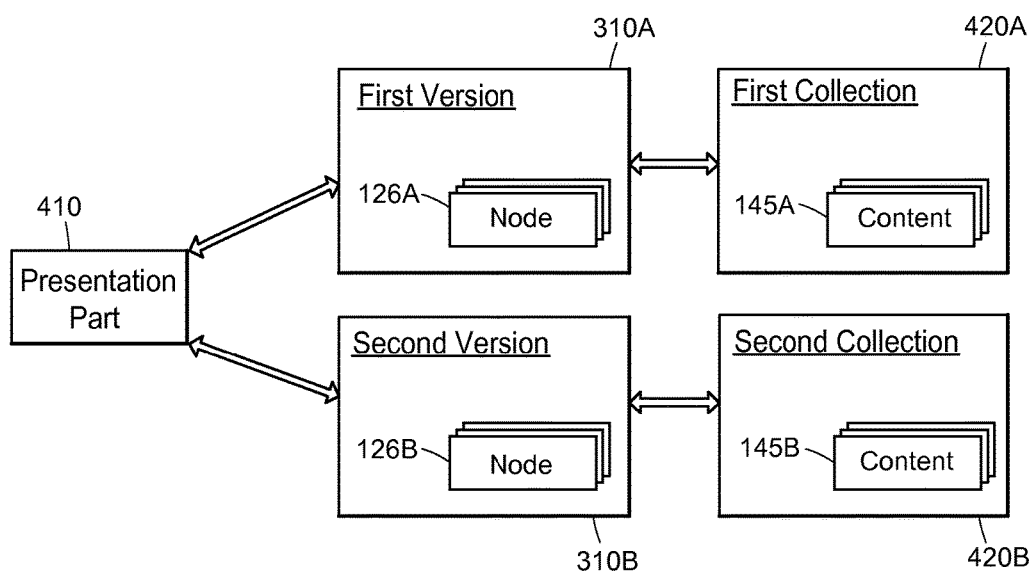
FIG. 4 depicts an example relational diagram, according to an embodiment.

FIG. 4 is a relational diagram 400 depicting relationships between various entities. In particular, the diagram 400 depicts relationships between entities associated with an example presentation part 410.

The presentation part 410 may represent an IMP, or at least a part of an IMP. For example, the part 410 may be an IMP, a program, a content block, a topic, a sequence, etc. While some parts of an IMP may have a single flow-definition, other parts of an IMP may have multiple flow-definitions. That is, some parts of an IMP may have multiple versions, wherein each version represents substantially the same information that needs to be presented to, or collected from, a user during presentation.

For example, the part 410 has two versions: a first version 310A and a second version 310B. The first version 310A and second version 310B may have different flow-definitions. That is, the two versions of the IMP 125A may include a different collection of nodes and/or a different flow between nodes. The flow-definitions for the first and second version 310A and 310B may be created via the flow interface 118 shown in FIGS. 1 and 3. The first and second version 310A and 310B may each represent a version of the part 410 that is tailored to a specific delivery-channel.

The first version 310A may include one or more nodes 126A, and the second version 310B may include one or more nodes 126B.

Generally speaking, the first version 310A corresponds to a first collection 420A of content assets 145A, and the second version 310B corresponds to a second collection 420B of content assets 145B. More particularly, the nodes 126A of the first version 310A may reference or include the content assets 145A, and the nodes 126B of the second version 310B may reference or include the content assets 145B.

VI. Example Methods 500A and 500B

Figure 5A:
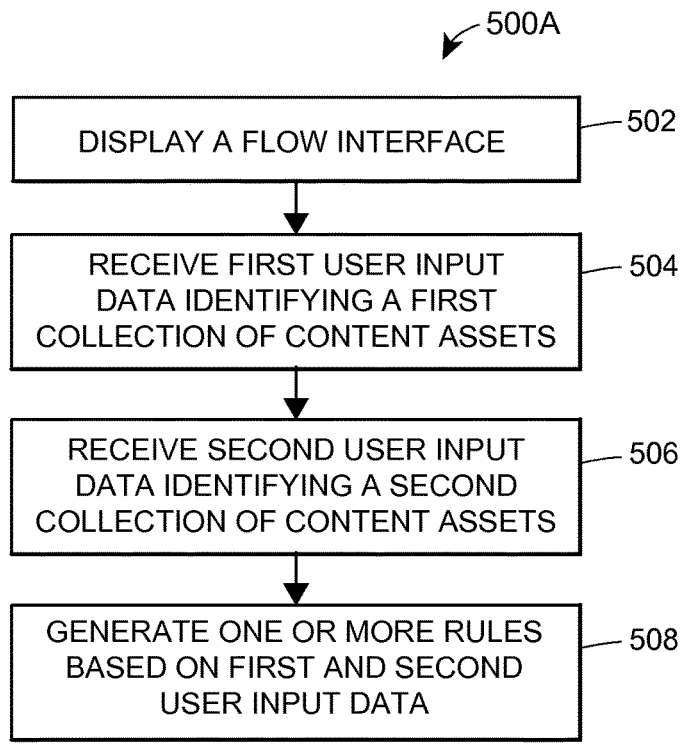
FIG. 5A depicts an example method for generating one or more rules for selecting a next content asset, according to an embodiment.

FIG. 5A depicts an example method 500A for generating one or more rules for selecting a next content asset to be presented during a presentation of an IMP. The method 500A may be implemented, in whole or in part, on one or more devices or systems such as those shown in the system 100 of FIG. 2 and the IMP Authoring System 600 of FIG. 6. In particular, the method 200A may be implemented by the IMP Authoring Tool 115 shown in FIG. 2 and/or the controller 610 shown in FIG. 6. The method may be saved as a set of instructions, routines, programs, or modules on memory, such as the memory device 633 or the memory device 655 shown in FIG. 6.

The method 500A begins when a flow interface 118 is displayed (block 502).

First user input data identifying a first collection of content assets may be received, e.g., by the IMP Authoring Tool 115 (block 504). The first user input data may be received at the controller 610 from the input device 639. A record of the first collection of content assets identified by the first user input may be stored to memory (e.g., the memory device 633 or the memory device(s) 655) so that the first collection of content assets are associated with a first version of at least part of an IMP ("first version of the IMP part"). The record may be created and/or stored to memory by the IMP Authoring Tool 115. The record may be subsequently referenced to facilitate presentation of the first version of the IMP part. For example (with reference to FIG. 2), to facilitate presentation of the first version of the IMP part, the rules engine 128 and/or content provision unit 129 may reference the record to determine which content from the content database 145 should be transmitted to the IMP Player 120 for presentation of the first version of the IMP part. In an embodiment, the first version of the IMP part may be associated with a delivery-channel. The record may include data identifying the delivery-channel associated with the first version of the IMP part (and thus with the first collection of content assets). In some instances, the rules 130 may indicate that the first version of the IMP part is to be presented when a first delivery-channel status is selected/active (which may be determined in some instances by referencing the delivery-channel status 136).

In an embodiment, the first input data may represent a node or collection of nodes selected by the user. For example, the user may select the node or collection of nodes by providing a flow-definition, such as the flow-definition 310 shown in FIG. 3. The selected node or collection of nodes may reference the first collection of content assets. For example, the first user input data may be or include data representing a collection of output-nodes. The output-nodes may include or reference the first collection of content assets so that when the pages corresponding to the output-nodes are presented (e.g., via a display device and/or audio device), the first collection of content assets are presented. Further, the first user input data may be or include data representing collection-nodes (e.g., sequences, topics, content blocks, etc.). The collection-nodes may include output-nodes that include or reference the first collection of content assets so that when the first version of the IMP part is presented, the first collection of content assets are presented.

The user may utilize the audio interface 116, visual interface 117, and/or flow interface 118 to identify the first collection of content assets. For example, the user may select the node or collection of nodes for the first version of the IMP part by dragging and dropping nodes or node templates (e.g., the previously described "stencils") onto a "flow design area" presented by the flow interface 118. The user may associate one or more content assets with a node by utilizing the audio interface 116 and/or the visual interface 117. For example, to edit or designate content (e.g., audio content assets or visual content assets) to be presented for a particular node when the first version of the IMP part is presented, the user may interact with the particular node in the flow interface 118 (e.g., by double clicking on the particular node; by single clicking on the particular node and selecting from a drop-down menu; etc.) to cause the audio interface 116, the visual interface 117, or both the audio interface 116 and visual interface 117 to be displayed. The user may then interact with the audio interface 116 to select audio content assets for the particular node, and/or may interact with the visual interface 117 to select visual content assets for the particular node. The audio interface 116 and visual interface 117, and the nature of how a user may interact with the audio interface 116 and visual interface 117, is described in more detail in Section III(C).

Second user input data identifying a second collection of content assets may be received, e.g., by the IMP Authoring Tool 115 (block 506). Like the first user input data, the second user input data may be received at the controller 610 from the input device 639, and may represent a node or collection of nodes. Further, a record of the second collection of content assets identified by the second user input may be stored to memory (e.g., the memory device 633 or the memory device(s) 655) so that the second collection of content assets are associated with a second version of at least part of the IMP ("second version of the IMP part"). The record associated with the second version of the IMP part may be similar to the record associated with the first version of the IMP part. In some embodiments, a common record may be used for the first and second version of the IMP part. Moreover, like the first input data, the second input data may represent a node or collection of nodes selected by the user. For example, the second user input data may be or include data representing a collection of nodes. Further, the user may utilize the audio interface 116, visual interface 117, and/or flow interface 118 to identify the second collection of content assets in a similar manner to that described with reference to the first collection of content assets.

One or more rules may be generated based on the first and second user input data (block 508). Depending on the embodiment, the one or more rules may be generated by the IMP Authoring Tool 115, the rules engine 128, or some other system. The one or more rules may be generated to include conditions for selecting the first version of the IMP part and/or conditions for selecting the second version of the IMP part. For example, the user may indicate, via interaction with the flow interface 118, that the first version is to be presented when a first delivery-channel is active, and that the second version is to be presented when a second delivery-channel is active. In such a scenario, one or more rules may be generated to reference the delivery-channel status 136, so that when the delivery-channel status 136 indicates that the first delivery-channel is active, the first version is presented; and when the delivery-channel status 136 indicates that the second delivery-channel is selected/active, the second version is presented.

Figure 5B:
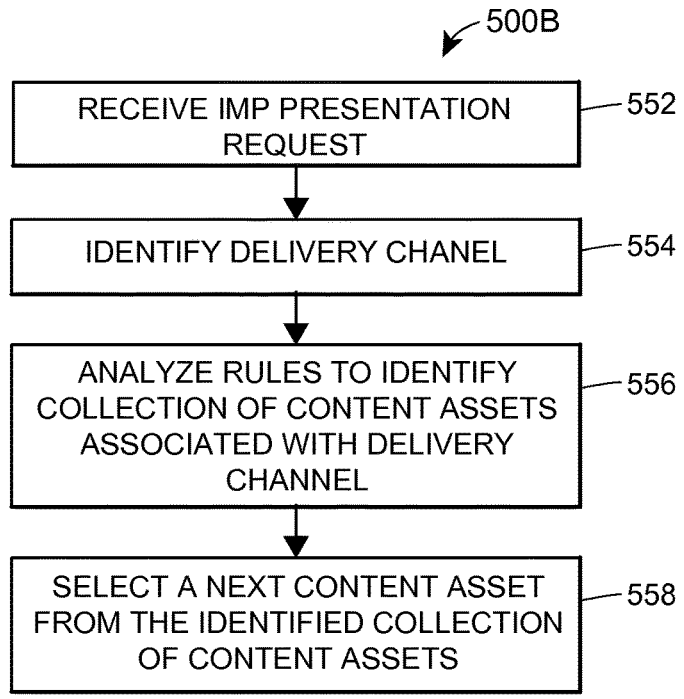
FIG. 5B depicts an example method for selecting a next content asset, according to an embodiment.

FIG. 5B depicts an example method 500B for selecting a next content asset to be presented during a presentation of an IMP. The method 500B may be implemented, in whole or in part, on one or more devices or systems such as those shown in the system 100 of FIG. 2 and the IMP Authoring System 600 of FIG. 6. In particular, the method 500B may be implemented by the rules engine 128 shown in FIG. 2 and/or the server(s) 620 shown in FIG. 6. The method may be saved as a set of instructions, routines, programs, or modules on memory, such as the memory device 655 shown in FIG. 6.

The method 500B begins when an IMP presentation request is received (block 552). The request may be received at the rules engine 128 and/or the servers 620.

A delivery-channel may be identified (block 554). Identifying a delivery-channel may include setting the delivery-channel status 136. For example, the delivery-channel status 136 may indicate whether the active delivery-channel is a web presentation, a desktop client presentation, a mobile application presentation, an email-based presentation, a text-message based presentation, etc. The delivery-channel status 136 may be set based on information received from the IMP Player 120 and/or client device 660. For example, the IMP Player 120 and/or client device 660 may transmit a delivery-channel identifier to a server 620, which may update the delivery-channel status 136 based on the received delivery-channel identifier.

Rules 130 may be analyzed to identify collection(s) of content assets associated with the identified delivery-channel (block 558). The rules 130 may be analyzed by the rules engine 128. The analyzed rules 130 may include one or more conditions indicating that a first collection of content assets should be presented when a first delivery-channel is active; and that a second collection of content assets should be presented when a second delivery-channel is active. For example, the rule 130 may indicate that a first version of an IMP part is to be presented when the first delivery-channel is active; and that a second version of the IMP part is to be presented when the second delivery-channel is active. To determine which delivery-channel is active, the delivery-channel status 136 shown in FIG. 1 may be referenced. The first version of the IMP part may include nodes referencing the first collection of content assets, while the second version of the IMP part may include nodes referencing the second collection of content assets. Thus, the appropriate collection of content assets may be identified by (i) identifying the active delivery-channel (e.g., by referencing the delivery-channel status 136), (ii) identifying a version associated with the active delivery-channel, (iii) identifying nodes for the version, and (iv) identifying the collection of content associated with the identified nodes.

A next content asset may be selected from the identified collection of content assets (block 558). For example, based on the identified active delivery-channel and the version associated with the active delivery-channel, the nodes of the identified version may be identified (and thus the collection of content assets associated with the nodes may be identified).

VII. An Example Imp Authoring System 600

Figure 6:
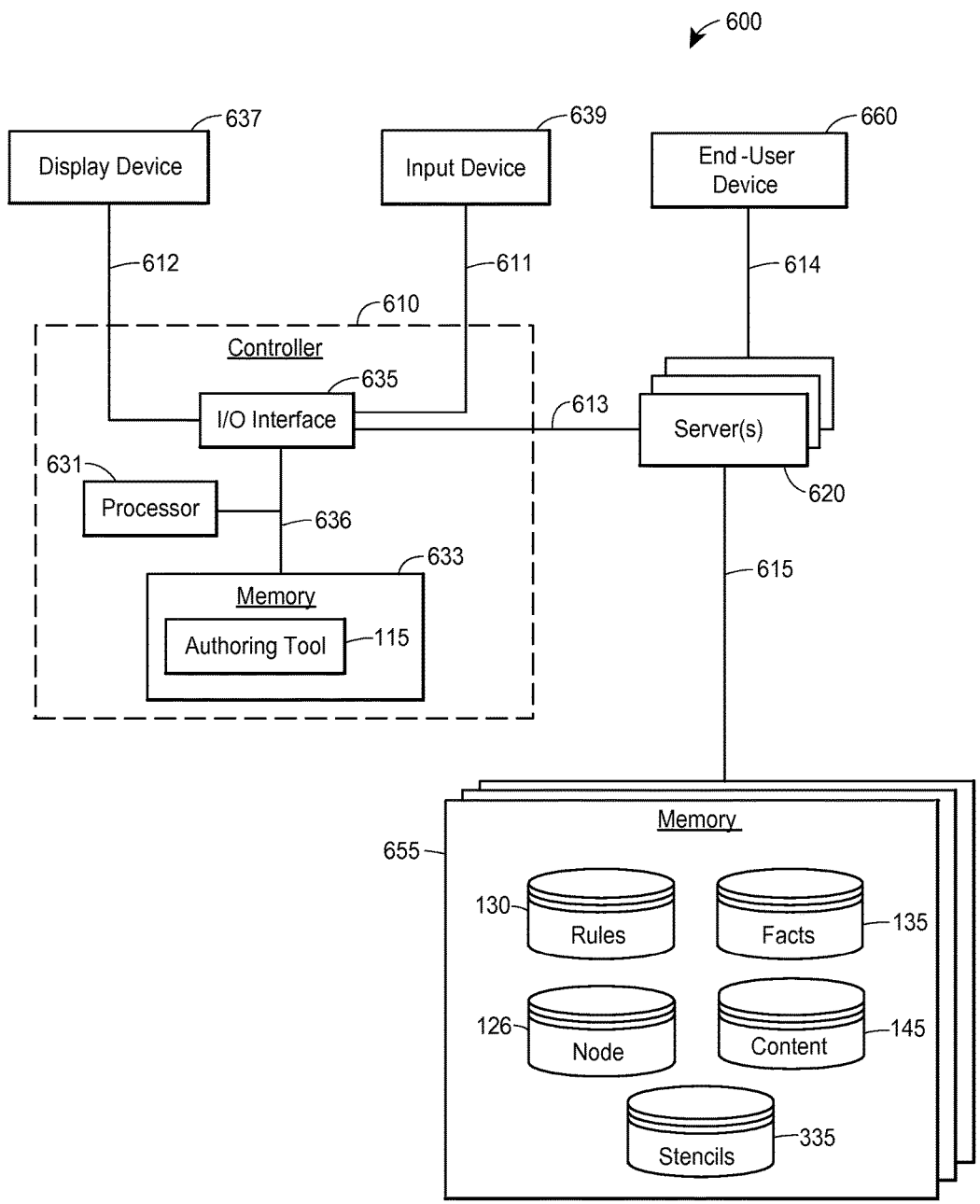
FIG. 6 depicts a block diagram of an example IMP Authoring System according to an embodiment.

FIG. 6 depicts a block diagram of an example IMP Authoring System 600 according to an embodiment. The IMP Authoring System 600 may include a controller 610, one or more display devices 637 (e.g., a screen or a monitor), one or more input devices 639 (e.g., touchscreen sensors, a mouse, keyboard, etc.), one or more servers 620, and one or more memory devices 655.

(A) Example Structure Associated with the Controller 610

The controller 610 may be communicatively connected to the input device 639 via the link 611, and may be communicatively connected to the display device 637 via the link 612. In an embodiment, the link 611 is wired in nature (e.g., a USB cable). In an embodiment, the link 611 is wireless in nature (e.g., a Bluetooth link). Similar to the link 611, the link 612 may be wired or wireless in nature depending on the embodiment. The controller 610 may be communicatively connected to the one or more servers 620 via the link 613. The link 613 may include one or more intermediary devices and links, some of which may be part of a network such as the network 110 shown in FIG. 2.

The controller 610 may include a processor 631, a memory device 633, and/or an I/O interface 635, each of which may be communicatively connected via a link 636. In an embodiment, the controller 610 includes multiple processors 631. In an embodiment, the link 636 is a system bus.

The memory 633 may store the IMP Authoring Tool 115 (described with reference to FIG. 2). The memory 633 may include one or more memory devices including computer-readable media, and may include volatile and/or non-volatile memory.

The I/O interface 635 may include one or more interfaces for sending and receiving data and/or instructions, such as a video interface, an input-interface, a communication-interface etc. The I/O interface 635 enables the controller 610 to establish a connection to other networks, systems, and/or devices. The I/O interface 635 may include a wireless interface (e.g., for establishing an RF connection, such as a Bluetooth connection) and/or a wired interface (e.g., for establishing connection via an Ethernet cable or USB cable).

In some embodiments, the functionality of the IMP Authoring System 600 is provided entirely by the controller 610. In such embodiments, the IMP Authoring System 600 may not include any of the servers 620.

(B) Example Structure Associated with the Server(s) 620

The one or more servers 620 may be communicatively connected to an end-user or client device 660 via a link 614, and may be communicatively connected to the one or more memory devices 655 via a link 615. Each of the links 614 and 615 may include one or more intermediary devices and links, some of which may be part of a network such as the network 110 shown in FIG. 2.

The memory device(s) 655 may store data representing rules 130, facts 135, nodes 126, content 145, and/or stencils 335. In an embodiment, the data in the knowledge base 140 shown in FIG. 2 is stored at one or more of the memory devices 655.

In some embodiments, the data representing one or more of the rules 130, facts 135, nodes 126, content 145, and/or stencils 335 may be stored at the memory device 633 of the controller 610.

(C) Example Operation Associated with the IMP Authoring System 600

In example operation, the processor 631 executes a set of instructions or routines representing the IMP Authoring Tool 115 to cause the controller 610 to provide a GUI (e.g., via the display device 637) for designing or creating an IMP 125. The provided GUI may include one or more of the audio interface 116, the visual interface 117, or the flow interface 118 shown in FIG. 2.

The controller 610 may cause the display device 637 to display the audio interface 116 shown in FIG. 2 to enable a designer to edit audio for a particular page in the IMP 125 (shown in FIG. 2). The controller 610 may receive input data from the one or more input devices 639. For example, the controller 610 may receive text-data from a keyboard. The controller 610 may utilize a text-to-speech tool (stored, e.g., at the memory device 633 or at the memory device 655) to convert the text-data to audio data. The audio data may then be stored to memory (e.g., as content data 145), and the controller 610 may store to memory page data (e.g., node data 126) for the edited page so that the page data references the audio data. Consequently, when the IMP 125 is later presented at the client device 660 and the edited page needs to be presented, one of the servers 620 (e.g., which may be implementing the rules engine 128 and/or the content provision unit 129 shown in FIG. 2) may reference the node data 126 to determine which audio file or data in the content database 145 should be transmitted to the client device 660 for presentation.

The controller 610 may cause the display device 637 to display the visual interface 117 shown in FIG. 2 to enable a designer to edit visual(s) for a particular page in the IMP 125. The controller 610 may receive input data from the one or more input devices 639. For example, the controller 610 may receive input-data from a mouse as the designer selects images from a library or file directory to be placed on the design area 205. Further, the controller 610 may receive text-data from a keyboard as a designer defines text to be displayed on the particular page. If the defined visuals are not already stored at the memory device(s) 655, the controller 610 may communicate with the servers 620 to store the visual data at the memory device(s) 655 as content data 145. The controller 610 may store to memory (e.g., at the memory device 655) page data (e.g., node data 126) for the edited page so that the page data references the defined visuals represented by the visual data. Consequently, when the IMP 125 is later presented at the client device 660 and the edited page needs to be presented, one of the servers 620 (e.g., which may be implementing the rules engine 128 or the content provision unit 129) can reference the node data 126 to determine which file or data in the content database 145 should be transmitted to the client device 660 for presentation.

The controller 610 may cause the display device 637 to display the flow interface 118 shown in FIG. 2 to enable a designer to define a flow between nodes of the IMP 125. The controller 610 may receive input data from the one or more input devices 639. For example, the controller 610 may receive input-data from a mouse as the designer drags and drops stencils 335 onto the design area 305 shown in FIG. 3 and defines a flow by connecting the created blocks. The controller 610 may then communicate with the server(s) 620 to store at the memory device data representing rules 130 and/or facts 135 generated based on the flow-definition created in the design area 305. In other words, the controller 610 may populate the knowledge base 140 based on the provided flow definition. Consequently, when the IMP 125 is later presented at the client device 660, one of the servers 620 can reference the rules 130 and/or facts 135 to determine a next node or nodes for presentation. In other words, the server 620 can references the rules 130 and/or facts 135 to determine, in or near real-time, nodes to be presented and an order for presenting the nodes.

Note, each stencil 335 may represent a template block. For example, the stencils 335 may include input-prompt stencils (e.g., a multiple-choice radio button input prompts), output stencils (e.g., page displays having a particular layout for presenting multimedia content), collection-node stencils (e.g., representing a program, edition, chapter, sequence, etc.), and/or decision stencils. Once a stencil 335 has been placed in the design area to create a new block, the designer may specify particular attributes or attribute values for the new block. For example, the designer may specify particular multimedia content to be presented (e.g., via a filename), specify particular questions to ask the end-user, etc.

It will be understood that in some embodiments, one or more of the various links connecting components of the IMP Authoring System 600 (i.e., links 611-615 and link 636) may include intermediary links or devices not shown in FIG. 6. For example, the link 613 between the controller 610 and the server(s) 620 may include intermediary routers, modems, switches, and other networking devices, as well as all of the communicative links between each of those intermediary devices. Further, each of the displayed links may include intermediary wireless links and/or intermediary wired links, depending on the embodiment.

VIII. Additional Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

(A) Systems(s)

As used herein, the term "entity" generally refers to something having a distinct existence. For example, depending on the context, a program or program element may be an entity. A particular data-set or piece of data may be an entity. A particular system or subsystem may be an entity. An object or device may be an entity. A piece of hardware or group of hardware may be an entity.

As used herein, the term "system" generally refers to a set of components or entities that form a whole, at least in some sense. Depending on the exact context, one or more of the components of the whole may interact with, or depend on, other components of the whole.

(B) Network(s)

As used herein, unless otherwise specified, the term "network" is a collection of nodes (e.g., devices or systems capable of sending, receiving and/or forwarding information) and links which are connected so as to enable telecommunication between the nodes.

Generally speaking, the term "node" (when used in reference to a network topology, and to be distinguished from the "nodes" discussed above in connection with FIGS. 1-8) refers to a connection point, redistribution point, or a communication endpoint. A node may be any device or system (e.g., a computer system) capable of sending, receiving and/or forwarding information. For example, end systems that originate and/or ultimately receive a message are nodes. Intermediary device that receive and forward the message are also generally considered to be "nodes."

A "link" is a pathway or medium connecting two or more nodes. A link may be a physical link and/or a logical link. A physical link is the interface and/or medium(s) over which information is transferred, and may be wired or wireless in nature. Examples of physicals links may include a cable with a conductor for transmission of electrical energy, a fiber optic connection for transmission of light, and/or a wireless electromagnetic signal that carries information via changes made to one or more properties of an electromagnetic wave(s).

A logical link between two or more nodes represents an abstraction of the underlying physical links and/or intermediary nodes connecting the two or more nodes. For example, two or more nodes may be logically coupled via a logical link. The logical link may be established via any combination of physical links and intermediary nodes (e.g., routers, switches, or other networking equipment).

A link is sometimes referred to as communication channel. In a wireless communication system a channel generally refers to a particular frequency or frequency band. A carrier signal (or carrier wave) is transmitted at the particular frequency or within the particular frequency band of the channel. In some instances, multiple signals may be transmitted over a single band/channel. For example, signals may sometimes be simultaneously transmitted over a single band/channel via different sub-bands or sub-channels. As another example, signals may sometimes be transmitted via the same band by allocating time slots over which respective transmitters and receivers use the band in question.

As already noted, a network is a collection of nodes and links. A network may include dedicated routers responsible for directing traffic between nodes, and, optionally, dedicated devices responsible for configuring and managing the network. Some or all of the nodes may be also adapted to function as routers in order to direct traffic sent between other network devices. Network devices may be interconnected in a wired or wireless manner, and network devices may have different routing and transfer capabilities. For example, dedicated routers may be capable of high volume transmissions while some nodes may be capable of sending and receiving relatively little traffic over the same period of time. Additionally, the connections between nodes on a network may have different throughput capabilities and different attenuation characteristics. A fiberoptic cable, for example, may be capable of providing a bandwidth several orders of magnitude higher than a wireless link because of the difference in the inherent physical limitations of the medium. A network may include networks or subnetworks, such as a local area network (LAN) or a wide area network (WAN).

(C) Communication Interface(s)

Some of the devices and/or systems described herein include a "communication interface" (sometimes referred to as a "network interface"). For example, the I/O interface 635 shown in FIG. 6 and the I/O interface 835 shown in FIG. 8 may each include a communication interface in some embodiments. A communication interface of a system enables the system (e.g., the controller 610 or client device 660) to send information to other system and/or receive information from other systems. In some instances, a communication interface of a system may be utilized to establish a direct connection to another system. In some instances, a communication interface of a system enables the system to connect to a network (via a link).

To illustrate, a communication interface can include circuitry for permitting wireless communication (e.g., short-range and/or long-range communication) with one or more devices or systems using any suitable communications protocol. For example, a communication interface may support Wi-Fi (e.g., an 802.11 protocol), Ethernet, Bluetooth, high frequency systems (e.g., 900 MHZ, 2.4 GHZ, and 5.6 GHZ communication systems), infrared, transmission control protocol/internet protocol ("TCP/IP") (e. g., any of the protocols used in each of the TCP/IP layers), hypertext transfer protocol ("HTTP"), BitTorrent, file transfer protocol ("FTP"), real-time transport protocol ("RTP"), real-time streaming protocol ("RTSP"), secure shell protocol ("SSH"), any other communications protocol, or any combination thereof. A communication interface of a system may also include circuitry that enables the system to be electrically or optically coupled to another device (e.g., via a coax cable or fiber optic cable) and communicate with that other device.

(D) Hardware and Software System(s)/Module(s)

Additionally, certain embodiments are described herein as including logic or a number of routines, subroutines, applications, or instructions. These may constitute either software (e.g., code embodied on a machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules/systems/subsystems of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

(E) Processor(s)

The various operations of example methods described herein may be performed, at least partially, by one or more processors. Such processors may be configured to fetch and execute instructions stored to memory. By executing these instructions, the processor can carry out various operations or functions.

The processors may be temporarily configured (e.g., by instructions or software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

(F) Memory and Computer-Readable Media

Generally speaking, as used herein the phrase "memory" or "memory device" may refer to any system or device including computer-readable media ("CRM"), which may be any available media accessible by the relevant computing system for placing, keeping, and/or retrieving information (e.g., data, computer-readable instructions, program modules, etc). The CRM may be implemented in any technology, device, or group of devices included in the relevant computing system or in communication with the relevant computing system. The CRM may include volatile and/or non-volatile media, and removable and/or non-removable media. The CRM may include, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store information and which can be accessed by the computing system. The CRM may be communicatively coupled to a system bus, enabling communication between the CRM and other systems or components coupled to the system bus. In some implementations the CRM may be coupled to the system bus via a memory interface (e.g., a memory controller). A memory interface is a circuit that manages the flow of data between the CRM and the system bus.

(G) System Bus(es)

Generally speaking, a processor or a particular system or subsystem may communicate with other components of the system or subsystem via one or more communication links. When communicating with components in a shared housing, for example, the processor may be communicatively connected to the components by a system bus. Unless stated otherwise, as used herein the phrase "system bus" refers to: a data bus (for carrying data), an address bus (for determining where the data should be sent), a control bus (for determining the operation to execute), or some combination thereof. Further, "system bus" may refer to any of several types of bus structures including a memory bus or memory controller, a peripheral bus, or a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

(H) Data/Information Generation and Manipulation

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

(I) Embodiments

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

(J) Relational and Logical Expressions

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

Although this detailed description contemplates various embodiments, it should be understood that the legal scope of the invention is defined by the words of the claims set forth at the end of this patent. This detailed description is to be construed as exemplary only and does not describe every possible embodiment, as describing every possible embodiment would be impractical, if not impossible. One could implement numerous alternate embodiments, using either current technology or technology developed after the filing date of this patent, which may fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims of this patent is referred to in this patent in a manner consistent with a single meaning, that is done for sake of clarity only so as to not confuse the reader, and it is not intended that such claim term be limited, by implication or otherwise, to that single meaning.

IX. Aspects

Embodiments of the techniques described in the present disclosure may include any number of the following aspects, either alone or combination:

1. A first system comprising: (a) a controller; (b) one or more memory devices communicatively coupled to the controller, the one or more memory devices storing one or more rules generated by the controller based on: (i) first user input data identifying a first collection of content assets for a first version of at least part of an interactive media pack ("IMP"), the first version to be presented when the IMP is presented via a first delivery-channel, and (ii) second user input data identifying a second collection of content assets for a second version of the at least part of the IMP, the second version to be presented when the IMP is presented via a second delivery-channel; and (c) one or more servers that are communicatively coupled to the one or more memory devices and that select a next content asset to be presented during a presentation of the IMP at a client device by performing an analysis of: (i) a delivery-channel status representing a delivery channel selected for the presentation of the IMP at the client device, and (ii) the one or more rules; wherein one or more servers: (i) select the next content asset from the first collection of content assets when the delivery channel status indicates that the first delivery channel has been selected, and (ii) select the next content asset from the second collection of content assets when the delivery channel status indicates that the second delivery channel has been selected.

2. The first system of the previous aspect, wherein the one or more rules specify that: (i) the first collection of content assets is associated with the first delivery channel, and (ii) the second collection of content assets is associated with the second delivery channel.

3. The first system of any of the previous aspects, wherein the one or more rules specify that (i) a first one or more nodes are associated with the first delivery-channel, and (ii) a second one or more nodes are associated with the second delivery-channel; wherein the first one or more nodes reference the first collection of content assets; and wherein the second one or more nodes reference the second collection of content assets.

4. The first system of any of the previous aspects, further including a server configured to transmit the selected next content asset to the client device.

5. The first system of any of the previous aspects, wherein the selected next content asset is: text, an image, a video, an animation, or some combination thereof.

6. The first system of any of aspects 1-4, wherein the selected next content asset is audio content.

7. The first system of any of the previous aspects, wherein the one or more servers include a rules engine, wherein the analysis of the delivery-channel status and of the one or more rules is performed by the rules engine.

8. The first system of any of the previous aspects, wherein the one or more servers include a content provision unit that transmits via the indicated delivery channel the selected next content asset for presentation.

9. The first system of any of the previous aspects, wherein the first delivery-channel is selected from a group comprising: emails, interactive voice response, a web-based player, or a dedicated application for IMP presentation; and wherein the second delivery-channel is a delivery-channel different from the first delivery-channel.

10. A first method comprising: receiving, at a controller, first user input data identifying a first collection of content assets for a first version of at least part of an interactive media pack ("IMP"), the first version to be presented when the IMP is presented via a first delivery-channel; receiving, at the controller, second user input data identifying a second collection of content assets for a second version of the at least part of the IMP, the second version to be presented when the IMP is presented via a second delivery-channel; based on the first user input data and the second user input data: generating by the controller one or more rules for selecting a next content asset to be presented during a presentation of the IMP; storing the one or more rules to one or more memory devices; analyzing (i) a delivery-channel status representing a delivery-channel selected for the presentation of the IMP, and (ii) the stored one or more rules; selecting the next content asset to be presented during the presentation of the IMP based on said analyzing, wherein: (i) the next content asset is selected from the first collection of content assets when the delivery channel status indicates that the first delivery channel has been selected, and (ii) the next content asset is selected from the second collection of content assets when the delivery channel status indicates that the second delivery channel has been selected.

11. The first method of the previous aspect, wherein the one or more rules specify that: (i) the first collection of content assets is associated with the first delivery channel, and (ii) the second collection of content assets is associated with the second delivery channel.

12. The first method of any of the previous aspects, wherein the one or more rules specify that (i) a first one or more nodes are associated with the first delivery-channel, and (ii) a second one or more nodes are associated with the second delivery-channel;

wherein the first one or more nodes reference the first collection of content assets; and wherein the second one or more nodes reference the second collection of content assets.

13. The first method of any of the previous aspects, further including transmitting the selected next content asset to the client device.

14. The first method of any of the previous aspects, wherein the selected next content asset is: text, an image, a video, an animation, or some combination thereof.

15. The first method of any of aspects 10-13, wherein the selected next content asset is audio content.

16. The first method of any of the previous aspects, wherein the first delivery-channel is selected from a group comprising: text messages, interactive voice response, a web-based player, or a dedicated application for IMP presentation; and wherein the second delivery-channel is a delivery-channel different from the first delivery-channel.

17. A second system comprising: (a) one or more memory devices storing a first collection of content assets associated with a first version of at least part of an interactive media pack ("IMP") and a second collection of content assets associated with a second version of at least part of an IMP; (b) one or more servers that are communicatively connected to the one or more memory devices and configured to: (i) analyze a delivery channel status to determine that a first delivery-channel has been selected for a presentation of the IMP; (ii) determine the stored first version is associated with the selected first delivery-channel; (iii) transmit one or more content assets from the first collection of content assets associated with the stored first version; (iv) based on transmitted one or more content assets from the first collection, storing progress data to track progress of the presentation of the IMP; (c) one or more client devices that are communicatively connected to the one or more servers, the one or more client devices configured to receive and present the one or more content assets from the first collection during the presentation of the IMP; wherein the one or more servers are further configured to: (i) analyze the delivery-channel status to determine that a second delivery-channel has been selected for the presentation of the IMP; (ii) determine the stored second version is associated with the second delivery-channel; (iii) analyze the stored progress data to determine a progress status for the presentation of the IMP; and (iv) transmit, based on the determined progress status, one or more content assets from the second collection of content assets associated with the identified second version so that the one or more content assets from the second collection may be presented during the presentation of the IMP; and wherein the one or more client devices are further configured to receive and present the one or more content assets from the second collection during the presentation of the IMP.

18. The second system of the previous aspect, wherein the one or more servers include a content provision unit, wherein the content provision unit is configured to perform the operation of transmitting the one or more content assets from the first collection and transmitting the one or more content assets from the second collection of content assets.

19. The second system of any of the previous aspects, wherein the first delivery-channel is selected from a group comprising: text messages, emails, a web-based player, or a dedicated application for IMP presentation; and wherein the second delivery-channel is a delivery-channel different from the first delivery-channel.

20. A second method comprising: analyzing, by one or more servers, a delivery-channel status to determine that a first delivery-channel has been selected for a presentation of an interactive media pack ("IMP"); identifying, by the one or more servers, a first version of at least part of the IMP, the first version associated with the selected first delivery-channel; transmitting, by the one or more servers, one or more content assets from a first collection of content assets associated with the identified first version so that the one or more content assets from the first collection may be presented during the presentation of the IMP; based on said transmitting of the one or more content assets from the first collection, storing progress data to track progress of the presentation of the IMP; analyzing, by the one or more servers, the delivery-channel status to determine that a second delivery-channel has been selected for the presentation of the IMP; identifying, by the one or more servers, a second version of at least part of the IMP, the second version associated with the second delivery-channel; analyzing, by the one or more servers, the stored progress data to determine a progress status for the presentation of the IMP; and transmitting, based on the determined progress status, one or more content assets from a second collection of content assets associated with the identified second version so that the one or more content assets from the second collection may be presented during the presentation of the IMP.

21. The second method of the previous aspect, wherein identifying the first version associated with the selected first delivery-channel comprises: analyzing one or more rules specifying that the first version is to be presented when the first delivery-channel is active; and wherein identifying the second version associated with the selected second delivery-channel comprises: analyzing one or more rules specifying that the second version is to be presented when the second delivery-channel is active.

22. A third system comprising: a means for receiving first user input data identifying a first collection of content assets for a first version of at least part of an interactive media pack ("IMP"), the first version to be presented when the IMP is presented via a first delivery-channel; a means for receiving second user input data identifying a second collection of content assets for a second version of the at least part of the IMP, the second version to be presented when the IMP is presented via a second delivery-channel; a means for generating, based on the first user input data and the second user input data, one or more rules for selecting a next content asset to be presented during a presentation of the IMP; a means for storing the one or more rules to one or more memory devices; a means for analyzing: (i) a delivery-channel status representing a delivery-channel selected for the presentation of the IMP, and (ii) the one or more rules; a means for selecting the next content asset to be presented during the presentation of the IMP based on said analyzing, wherein: (i) the next content asset is selected from the first collection of content assets when the delivery channel status indicates that the first delivery channel has been selected, and (ii) the next content asset is selected from the second collection of content assets when the delivery channel status indicates that the second delivery channel has been selected.

23. The third system of the previous aspect, wherein the means for receiving first user input data identifying a first collection of content assets for a first version of at least part of an IMP is one or more of: the authoring tool 115, the audio interface 116, the visual interface 117, the flow interface 118, the display device 637, the input device 639, and/or the controller 610.

24. The third system of any of the previous aspects, wherein the means for receiving second user input data identifying a second collection of content assets for a second version of the at least part of the IMP is one or more of: the authoring tool 115, the audio interface 116, the visual interface 117, the flow interface 118, the display device 637, the input device 639, and/or a controller 610.

25. The third system of any of the previous aspects, wherein the means for generating the one or more rules for selecting a next content asset to be presented during a presentation of the IMP is one or more of: the IMP Authoring Tool 115, the rules engine 128, the controller 610, and/or one of the servers 620.

26. The third system of any of the previous aspects, wherein the means for storing the one or more rules to one or more memory devices is one or more of: the rules engine 128, the knowledge base 140, the IMP Authoring Tool 115, the controller 610, one or more of the servers 620, and/or one or more of the memory devices 655.

27. The third system of any of the previous aspects, wherein the means for analyzing: (i) the delivery-channel status representing the delivery-channel selected for the presentation of the IMP, and (ii) the one or more rules is one or more of: the rules engine 128 and/or one or more of the servers 620.

28. The third system of any of the previous aspects, wherein the means for selecting the next content asset to be presented during the presentation of the IMP is one or more of: the rules engine 128, the content provision unit 129, monitor 127, the progress data 141, the database 124, the content database 145, one or more of the servers 620, and/or one or more of the memory devices 655.

29. The third system of any of the previous aspects, wherein the presentation of the IMP occurs via one or more of: the IMP Player 120 and/or the client device 660.

30. The third system of any of the previous aspects, wherein the delivery-channel selected for the presentation of the IMP is one or more of: text messaging, emailing, interactive voice response, a web-based player, and/or a dedicated application.

31. A fourth system comprising: a means for analyzing a delivery-channel status to determine that a first delivery-channel has been selected for a presentation of an interactive media pack ("IMP"); a means for identifying a first version of at least part of the IMP, the first version associated with the selected first delivery-channel; a means for transmitting one or more content assets from a first collection of content assets associated with the identified first version so that the one or more content assets from the first collection may be presented during the presentation of the IMP; a means for storing progress data to track progress of the presentation of the IMP, said storing based on the transmitted one or more content assets from the first collection; a means for analyzing the delivery-channel status to determine that a second delivery-channel has been selected for the presentation of the IMP; a means for identifying a second version of at least part of the IMP, the second version associated with the second delivery-channel; a means for analyzing the stored progress data to determine a progress status for the presentation of the IMP; and a means for transmitting one or more content assets from a second collection of content assets associated with the identified second version so that the one or more content assets from the second collection may be presented during the presentation of the IMP.

32. The fourth system of the previous aspect, wherein the means for analyzing the delivery-channel status to determine that the first delivery-channel has been selected for the presentation of the IMP is one or more of: rules engine 128, the knowledge base 140, the delivery-channel status 136, one or more of the servers 620, and/or one or more of the memory devices 655.

33. The fourth system of any of the previous aspects, wherein the means for identifying the first version of at least part of the IMP is one or more of: the database 124, the knowledge base 140, the delivery-channel status 136, the rules engine 128, one or more of the servers 620, and/or one or more of the memory device 655.

34. The fourth system of any of the previous aspects, wherein the means for transmitting one or more content assets from the first collection of content assets associated with the identified first version so that the one or more content assets from the first collection may be presented during the presentation of the IMP is one or more of: the rules engine 128, the content provision unit 129, the content database 145, one or more of the servers 620, and/or one or more of the memory devices 655.

35. The fourth system of any of the previous aspects, wherein the means for storing progress data to track progress of the presentation of the IMP is one or more of: the monitor 127, the progress data 141, the presentation 150, the presentation ID 151, the progress status 152, one or more of the servers 620, and/or one or more of the memory devices 655.

36. The fourth system of any of the previous aspects, wherein the means for analyzing the delivery-channel status to determine that a second delivery-channel has been selected for the presentation of the IMP is one or more of: the rules engine 128, the knowledge base 140, the rules 130, the facts 135, the delivery-channel status 136, one or more of the servers 620, and/or one or more of the memory devices 655.

37. The fourth system of any of the previous aspects, wherein the means for identifying the second version of at least part of the IMP, the second version associated with the second delivery-channel is one or more of: the rules engine 128, the knowledge base 140, the rules 130, the facts 135, the delivery-channel status 136, the database 124, one or more of the nodes 126, the version ID 131, one or more of the servers 620, and/or one or more of the memory devices 655.

38. The fourth system of any of the previous aspects, wherein the means for analyzing the stored progress data to determine the progress status for the presentation of the IMP is one or more of: the monitor 127, the progress data 141, the progress status 152, the rules engine 128, one or more of the servers 620, and/or one or more of the memory devices 655.

39. The fourth system of any of the previous aspects, wherein the means for transmitting one or more content assets from the second collection of content assets associated with the identified second version so that the one or more content assets from the second collection may be presented during the presentation of the IMP include one or more of: the content provision unit 129, the rules engine 128, the content database 145, one or more of the servers 620, and/or one or more of the memory devices 655.

40. The fourth system of any of the previous aspects, wherein the presentation of the IMP occurs via one or more of: the IMP Player 120 and/or the client device 660.

41. The fourth system of any of the previous aspects, wherein the first delivery-channel is one or more of: text messaging, emailing, interactive voice response, a web-based player, and/or a dedicated application.

42. The fourth system of any of the previous aspects, wherein the second delivery-channel is one or more of: text messaging, emailing, interactive voice response, a web-based player, and/or a dedicated application.

The invention claimed is:

1. A system comprising:
   (a) a controller;
   (b) one or more memory devices communicatively coupled to the controller, the one or more memory devices storing one or more rules for presenting an interactive media pack ("IMP") via one of a plurality of delivery-channels each corresponding to a type of user-interface by which the IMP is presentable, the one or more rules generated by the controller based on:
      (i) first user input data identifying a first set of nodes, representing a first version of at least part of the IMP, selected to be presented when a first delivery-channel is active, wherein the first set of nodes references a first collection of content assets, and
      (ii) second user input data identifying a second set of nodes, representing a second version of the at least part of the IMP, selected to be presented when a second delivery-channel distinct from the first delivery-channel is active, wherein the second set of nodes is distinct from the first set of nodes and references a second collection of content assets; and
   (c) one or more servers that are communicatively coupled to the one or more memory devices and that select a next content asset to be presented during a presentation of the IMP at a client device by performing an analysis of:

(i) a delivery-channel status representing a delivery-channel selected for the presentation of the IMP at the client device, and (ii) the one or more rules generated by the controller;

wherein the one or more servers: (i) select the next content asset from the first collection of content assets when the delivery-channel status indicates that the first delivery-channel has been selected, and (ii) select the next content asset from the second collection of content assets when the delivery-channel status indicates that the second delivery-channel has been selected.

2. The system of claim 1, wherein the one or more rules specify that: (i) the first collection of content assets is associated with the first delivery-channel, and (ii) the second collection of content assets is associated with the second delivery-channel.

3. The system of claim 1, further including a server configured to transmit the selected next content asset to the client device.

4. The system of claim 1, wherein the selected next content asset is: text, an image, a video, an animation, or some combination thereof.

5. The system of claim 1, wherein the selected next content asset is audio content.

6. The system of claim 1, wherein the one or more servers include a rules engine, wherein the analysis of the delivery-channel status and of the one or more rules is performed by the rules engine.

7. The system of claim 1, wherein the one or more servers include a content provision unit that transmits via the indicated delivery-channel the selected next content asset for presentation.

8. The system of claim 1, wherein the first delivery-channel is selected from a group comprising: emails, interactive voice response, a web-based player, or a dedicated application for IMP presentation; and wherein the second delivery-channel is a delivery-channel different from the first delivery-channel.

9. A method for presenting an interactive media pack ("IMP") by way of multiple delivery-channels, the method comprising:

receiving, at a controller, first user input data identifying a first set of nodes that represents a first version of at least part of an IMP and that has been selected to be presented when a first delivery-channel is active, wherein the first set of nodes references a first collection of content assets;

receiving, at the controller, second user input data identifying a second set of nodes that represents a second version of the at least part of the IMP and that has been selected to be presented when a second delivery-channel distinct from the first delivery-channel is active, wherein the second set of nodes is distinct from the first set of nodes and references a second collection of content assets;

based on the first user input data and the second user input data: generating by the controller one or more rules for selecting a next content asset to be presented during a presentation of the IMP;

storing the one or more rules to one or more memory devices;

analyzing (i) a delivery-channel status representing a delivery-channel selected for the presentation of the IMP, and (ii) the stored one or more rules;

selecting the next content asset to be presented during the presentation of the IMP based on said analyzing, wherein: (i) the next content asset is selected from the first collection of content assets when the delivery-channel status indicates that the first delivery-channel has been selected, and (ii) the next content asset is selected from the second collection of content assets when the delivery-channel status indicates that the second delivery-channel has been selected.

10. The method of claim 9, wherein the one or more rules specify that: (i) the first collection of content assets is associated with the first delivery-channel, and (ii) the second collection of content assets is associated with the second delivery-channel.

11. The method of claim 9, further including transmitting the selected next content asset to the client device.

12. The method of claim 9, wherein the selected next content asset is: text, an image, a video, an animation, or some combination thereof.

13. The method of claim 9, wherein the selected next content asset is audio content.

14. The method of claim 9, wherein the first delivery-channel is selected from a group comprising: text messages, interactive voice response, a web-based player, or a dedicated application for IMP presentation; and wherein the second delivery-channel is a delivery-channel different from the first delivery-channel.

15. A system for presenting an interactive media pack ("IMP") by way of multiple delivery-channels, the system comprising:

(a) one or more memory devices storing: (i) a first set of nodes, representing a first version of at least part of an IMP, selected to be presented when a first delivery-channel is active, wherein the first set of nodes references a first collection of content assets, and (ii) a second set of nodes, representing a second version of the at least part of the IMP, selected to be presented when a second delivery-channel distinct from the first delivery-channel is active, wherein the second set of nodes is distinct from the first set of nodes and references a second collection of content assets;

(b) one or more servers that are communicatively connected to the one or more memory devices and configured to:

(i) analyze a delivery-channel status to determine that a first delivery-channel has been selected for a presentation of the IMP;

(ii) determine the stored first version is associated with the selected first delivery-channel;

(iii) transmit one or more content assets from the first collection of content assets associated with the stored first version; and (iv) based on the transmitted one or more content assets from the first collection, storing progress data to track progress of the presentation of the IMP; and (c) one or more client devices that are communicatively connected to the one or more servers, the one or more client devices configured to receive and present the one or more content assets from the first collection during the presentation of the IMP;

wherein the one or more servers are further configured to:

(i) analyze the delivery-channel status to determine that a second delivery-channel has been selected for the presentation of the IMP;

(ii) determine the stored second version is associated with the second delivery-channel;

(iii) analyze the stored progress data to determine a progress status for the presentation of the IMP; and (iv) transmit, based on the determined progress status, one or more content assets from the second collection of content assets associated with the identified second version so that the one or more content assets from the second collection may be presented during the presentation of the IMP;

wherein the one or more client devices are further configured to receive and present the one or more content assets from the second collection during the presentation of the IMP.

16. The system of claim 15, wherein the one or more servers include a content provision unit, wherein the content provision unit is configured to perform the operation of transmitting the one or more content assets from the first collection and transmitting the one or more content assets from the second collection of content assets.

17. The system of claim 15, wherein the first delivery-channel is selected from a group comprising: text messages, emails, a web-based player, or a dedicated application for IMP presentation; and wherein the second delivery-channel is a delivery-channel different from the first delivery-channel.

18. A method comprising:

analyzing, by one or more servers, a delivery-channel status to determine that a first delivery-channel has been selected for a presentation of an interactive media pack ("IMP");

identifying, by the one or more servers, a first set of nodes that represents a first version of at least part of an IMP and that has been selected to be presented when the first delivery-channel is active transmitting, by the one or more servers, one or more content assets from a first collection of content assets associated with the identified first version so that the one or more content assets from the first collection may be presented during the presentation of the IMP;

based on said transmitting of the one or more content assets from the first collection, storing progress data to track progress of the presentation of the IMP;

analyzing, by the one or more servers, the delivery-channel status to determine that a second delivery-channel has been selected for the presentation of the IMP;

identifying, by the one or more servers, a second set of nodes that represents a second version of the at least part of the IMP and that has been selected to be presented when a second delivery-channel distinct from the first delivery-channel is active;

analyzing, by the one or more servers, the stored progress data to determine a progress status for the presentation of the IMP; and transmitting, based on the determined progress status, one or more content assets from a second collection of content assets associated with the identified second version so that the one or more content assets from the second collection may be presented during the presentation of the IMP.

19. The method of claim 18, wherein identifying the first version associated with the selected first delivery-channel comprises: analyzing one or more rules specifying that the first version is to be presented when the first delivery-channel is active; and wherein identifying the second version associated with the selected second delivery-channel comprises: analyzing one or more rules specifying that the second version is to be presented when the second delivery-channel is active.

* * * * *